United States Patent
Jha et al.

(10) Patent No.: US 12,281,353 B1
(45) Date of Patent: Apr. 22, 2025

(54) TEREPHTHALATE BIOSENSORS AND USES THEREOF

(71) Applicants: Triad National Security, LLC, Los Alamos, NM (US); University of Georgia Research Foundation Inc., Athens, GA (US)

(72) Inventors: Ramesh K. Jha, Los Alamos, NM (US); Taraka T. Dale, Los Alamos, NM (US); Ryan E. Bermel, Los Alamos, NM (US); Ellen Lee Neidle, Athens, GA (US)

(73) Assignees: TRIAD NATIONAL SECURITY, LLC, Los Alamos (MX); UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 43 days.

(21) Appl. No.: 17/173,065

(22) Filed: Feb. 10, 2021

Related U.S. Application Data

(60) Provisional application No. 62/972,365, filed on Feb. 10, 2020.

(51) Int. Cl.
*C12Q 1/6825* (2018.01)
*C07K 14/47* (2006.01)
*C12Q 1/6853* (2018.01)
*G01N 33/58* (2006.01)

(52) U.S. Cl.
CPC ........ *C12Q 1/6825* (2013.01); *C07K 14/4702* (2013.01); *C12Q 1/6853* (2013.01); *G01N 33/582* (2013.01)

(58) Field of Classification Search
CPC .............. C12Q 1/6825; C12Q 1/6853; C07K 14/4702; G01N 33/582
See application file for complete search history.

(56) References Cited

PUBLICATIONS

Sasoh( Applied and Environmental Microbiology, Mar. 2006, p. 1825-1832).*
Kasai (Applied and Environmental Microbiology, Sep. 2010, p. 6047-6055).*
GenBank Accession AB238678.1 (https://www.ncbi.nlm.nih.gov/nuccore/78210734?sat=3&satkey=36993984, Jul. 26, 2016).*
Elliot (IUBMB Life, 63(12): 1075-1080, Dec. 2011).*
Charles Daniel Murin et al., "Expression Vectors for Acinetobacter baylyi ADP1," Applied and Environmental Microbiology, 78(1):280-283, (Jan. 2012).
Jamie E. Prior et al., "Broad-Host-Range Vectors for Protein Expression Across Gram Negative Hosts," Biotechnology and Bioengineering, 106(2):326-332, (Jun. 2010).
Masaru Hosaka et al., "Novel Tripartite Aromatic Acid Transporter Essential for Terephthalate Uptake in Comamonas sp. Strain E6," Applied and Environmental Microbiology, 79(19):6148-6155, (Oct. 2013).
Melissa Tumen-Velasquez et al., "Accelerating pathway evolution by increasing the gene dosage of chromosomal segments," PNAS, 115(27):7105-7110, (Jul. 2018).
Michael D. Lynch et al., "Broad Host Range Vectors for Stable Genomic Library Construction," Biotechnology and Bioengineering, 94(1):151-158, (May 2006).
Ramesh K. Jha et al., "Engineering an Acinetobacter regulon for biosensing and high-throughput enzyme screening in *E. coli* via flow cytometry," Nucleic Acids Research, 42(12):8150-8160, (2014).
Ramesh K. Jha et al., "Smart Microbial Cells Couple Catalysis and Sensing to Provide High-Throughput Selection of an Organophosphate Hydrolase," American Chemical Society Synthetic Biology, 9:1234-1239, (2020).

* cited by examiner

*Primary Examiner* — Steven Pohnert
(74) *Attorney, Agent, or Firm* — Alston & Bird LLP

(57) ABSTRACT

Biosensors for detection terephthalic acid (TPA) and methods of their use are provided. The biosensors include a nucleic acid encoding a TphR protein, a promoter regulated by TPA, and a reporter operably linked to the promoter. Vectors and host cells including the biosensors are also provided.

13 Claims, 20 Drawing Sheets

Specification includes a Sequence Listing.

```
5'... tagcggccgctgcaggcctcagggcccgatcgatgccgccgcttaattaattaat
     ++++++++++++++++++++++++++++++++++++++++++++++++++++++++  55
3'   atcgccggcgacgtccggagtcccgggctagctacggcggcgaattaattaatta
     [ BioBrick suffix ]

ccagaggcatcaaataaaacgaaaggctcagtcgaaagactgggcctttcgtttt
     ++++++++++++++++++++++++++++++++++++++++++++++++++++++++  110
     ggtctccgtagtttattttgctttccgagtcagctttctgacccggaaagcaaaa
            [          rrnB T1 terminator          ]

atctgttgtttgtcggtgaacgctctcctgagtaggacaaatccgccgccctaga
     ++++++++++++++++++++++++++++++++++++++++++++++++++++++++  165
     tagacaacaaacagccacttgcgagaggactcatcctgtttaggcggcgggatct
        [    rrnB T1 terminator    ]

cctagtgtcatttatttccccgtttcagcatcaagaacctttgcataacttgc
     ++++++++++++++++++++++++++++++++++++++++++++++++++++++++  220
     ggatcacagtaaaataaagggggcaaagtcgtagttcttggaaacgtattgaacg
              230         225          220
           ▪  K  I  E  G  T  E  A  D  L  V  K  A  Y  S  A
           <////////////////// repA ////////////////// tctatatccacactgataattgccctcaaaccataatctaaaggcgctagagttt
     ++++++++++++++++++++++++++++++++++++++++++++++++++++++++  275
     agatataggtgtgactattaacgggagtttggtattagatttccgcgatctcaaa
          215         210         205         200
       R  Y  G  C  Q  Y  N  G  E  F  W  L  R  F  A  S  S  N
       <////////////////// repA ////////////////// gttgaaacaatatcttttacatcattcgtatttaaaattccaaactccgctcccc
     ++++++++++++++++++++++++++++++++++++++++++++++++++++++++  330
     caactttgttatagaaaatgtagtaagcataaattttaaggtttgaggcgagggg
           195         190         185
       T  S  V  I  D  K  V  D  N  T  N  L  I  G  F  E  A  G  R
       <////////////////// repA ////////////////// taaggcgaataaaagccattaaatcttttgtatttaccaaattatagtcatccac
     ++++++++++++++++++++++++++++++++++++++++++++++++++++++++  385
     attccgcttattttcggtaatttagaaaacataaatggtttaatatcagtaggtg
          180         175         170         165
       L  R  I  F  A  M  L  D  K  T  N  V  L  N  Y  D  D  V
       <////////////////// repA ////////////////// tatatctaagagtaaattcttcaattctcttttttggctttcatcaagtgttata
     ++++++++++++++++++++++++++++++++++++++++++++++++++++++++  440
     atatagattctcatttaagaagttaagagaaaaaaccgaaagtagttcacaatat
          160         155         150         145
       I  D  L  L  L  N  K  L  E  R  K  Q  S  E  D  L  T  I
       <////////////////// repA //////////////////
```

FIG. 7A

```
tagcggtcaatatcaaaatcattaatgttcaaaatatcttttttgtcgtatatat
++++++++++++++++++++++++++++++++++++++++++++++++++++++++
atcgccagttatagttttagtaattacaagttttatagaaaaaacagcatatata
         140            135            130
  V  R  D  I  D  F  D  N  I  N  L  I  D  K  K  D  Y  I  H
< ///////////////////////// repA ///////////////////////// gtttattcttagcaatagcgtcctttgattcatgagtcaaatattcatatgaacc
++++++++++++++++++++++++++++++++++++++++++++++++++++++++
caaataagaatcgttatcgcaggaaactaagtactcagtttataagtatacttgg
      125            120            115            110
  K  N  K  A  I  A  D  K  S  E  H  T  L  Y  E  Y  S  G
< ///////////////////////// repA ///////////////////////// tttgatataatcaagtatctcaacatgagcaactgaactattccccaattttcgc
++++++++++++++++++++++++++++++++++++++++++++++++++++++++
aaactatattagttcatagagttgtactcgttgacttgataaggggttaaaagcg
      105            100             95             90
  K  I  Y  D  L  I  E  V  H  A  V  S  S  N  G  L  K  R
< ///////////////////////// repA ///////////////////////// ttaatcttgttcctaacgctttctattgttacaggatttcgtgcaatatatataa
++++++++++++++++++++++++++++++++++++++++++++++++++++++++
aattagaacaaggattgcgaaagataacaatgtcctaaagcacgttatatatatt
       85             80             75
  K  I  K  N  R  V  S  E  I  T  V  P  N  R  A  I  Y  I  V
< ///////////////////////// repA ///////////////////////// cgtgatagtgtggttttttatagtgctttccatttcgtataacatcactactatt
++++++++++++++++++++++++++++++++++++++++++++++++++++++++
gcactatcacaccaaaaaatatcacgaaaggtaaagcatattgtagtgatgataa
       70             65             60             55
  H  Y  H  P  K  K  Y  H  K  G  N  R  I  V  D  S  S  N
< ///////////////////////// repA ///////////////////////// ccatgtatctttatcttttttttcgtccatatcgtgtaaaggactgacagccata
++++++++++++++++++++++++++++++++++++++++++++++++++++++++
ggtacatagaaatagaaaaaaaagcaggtatagcacatttcctgactgtcggtat
       50             45             40             35
  W  T  D  K  D  K  K  E  D  M  D  H  L  P  S  V  A  M
< ///////////////////////// repA ///////////////////////// gatacgcccaaactctctaattttccttccaatcattaggaattgagtcaggat
+++++++++++++++++++++++++++++++++++++++++++++++++++++++
ctatgcgggtttgagagattaaaaggaaggttagtaatccttaactcagtccta
       30             25             20
  S  V  G  L  S  E  L  K  E  K  W  D  N  P  I  S  D  P  Y
< ///////////////////////// repA /////////////////////////
```

```
ataataaaaatccaaaatttctagctttagtattttaatagccatgatataatt
tattattttaggttttaaagatcgaaatcataaaaattatcggtactatattaa
        15        10        5         1
         L  L  F  G  F  N  R  A  K  T  N  K  I  A  M
         <////////////repA////////////
```
880

```
acctcatcaaaaacaagtagcgaaaactcgtatccttctaaaaacgcgagctttc
tggaatagtttttgttcatcgcttttgagcataggaagatttttgcgctcgaaag
```
935

```
gctatttttttgttctgattcctttcttcgatattcttctatagctaacgccg
cgaataaaaaaaacaagactaaggaaagaacgtataagaagatatcgattgcggc
             50        45        40
         ■  K  K  Q  E  S  E  K  R  A  Y  E  E  I  A  L  A  A
         ////////Hypothetical protein///////
```
990

```
caaccgcagattttgaaaaaccttttgtttcgccatatctgttaattttttatc
gttggcgtctaaaacttttggaaaaacaaagcggtatagacaattaaaaaatag
        35        30        25        20
         V  A  S  K  S  F  G  K  Q  K  A  M  D  T  L  K  K  D
         <////////Hypothetical protein////////
```
1045

```
ttgctcttttgtcagagaaatcataactctttttttcgattctgaaatcaccatt
aacgagaaaacagtctctttagtattgagaaaaaaagctaacactttagtggtaa
        15        10        5         1
         Q  E  K  T  L  S  I  M  V  R  K  K  S  E  S  I  V  M
         <////////Hypothetical protein////////
```
1100

```
taaaaaactccaatcaaataatttataaagttagtgtatcactttgtaatcata
attttttgaggttagtttattaaatatttcaatcacatagtgaaacattagtat
                                              70
                                           ■  K  T  I  M
                                           <//Hypothetical protein/
```
1155

```
aaaacaacaataaagctacttaaatatagatttataaaaaacgttggcgaaaacg
ttttgttgttatttcgatgaattttatctaaatatttttttgcaaccgcttttgc
 65        60        55        50
  F  V  V  I  F  S  S  L  Y  L  N  I  F  F  T  P  S  F  T
  <////////Hypothetical protein////////
```
1210

FIG. 7C

```
ttggcgattcgttggcgattgaaaaaccccttaaacccttgagccagttgggata
++++++++++++++++++++++++++++++++++++++++++++++++++++++++    1265
aaccgctaagcaaccgctaacttttggggaatttgggaactcggtcaaccctat
     45        40         35         30
   P  S  E  N  A  I  S  F  G  R  L  G  K  L  W  N  P  Y
<////////////////Hypothetical protein///////////////// gagcgttttggcacaaaaattggcactcggcacttaatggggggtcgtagtacg
++++++++++++++++++++++++++++++++++++++++++++++++++++++++    1320
ctcgcaaaaaccgtgttttttaaccgtgagccgtgaattaccccccagcatcatgc
          25         20         15
   L  T  K  P  V  F  I  P  V  R  C  K  I  P  P  R  L  V
<////////////////Hypothetical protein///////////////// gaagcaaaattcgcttcctttccccccattttttttccaaattccagattttttc
++++++++++++++++++++++++++++++++++++++++++++++++++++++++    1375
cttcgttttaagcgaaggaaagggggggtaaaaaaaggtttaaggtctaaaaaaag
   10          5           1
   S  A  F  N  A  E  K  G  G  M
<////////////////Hypothetical protein///// aaaaattttccagcgctaccgctcggcaaaattgcaagcaattttttaaaatcaaa
++++++++++++++++++++++++++++++++++++++++++++++++++++++++    1430
ttttttaaaaggtcgcgatggcgagccgttttaacgttcgttaaaaattttagttt cccatgagggaatttcattccctcatactcccttgagcctcctccaaccgaaata
++++++++++++++++++++++++++++++++++++++++++++++++++++++++    1485
gggtactcccttaaagtaagggagtatgagggaactcggaggaggttggctttat
                                                    1
                                                    |
                                                  ⊠>
                                              Factor Xa site gaagggcgctgcgcttattatttcattcagtcatcggctttcataatctaacaga
++++++++++++++++++++++++++++++++++++++++++++++++++++++++    1540
cttcccgcgacgcgaataataaagtaagtcagtagccgaaagtattagattgtct E  G  R  C  A  Y  Y  F  I  Q  S  S  A  F  I  I ■
⊠>------ (in frame with Factor Xa site) ---------->
Factor Xa site caacatcttcgctgcaaagccacgctacgctcaagggcttttacgctacgataac
++++++++++++++++++++++++++++++++++++++++++++++++++++++++    1595
gttgtagaagcgacgtttcggtgcgatgcgagttcccgaaaatgcgatgctattg gcctgttttaacgattatgccgataactaaacgaaataaacgctaaaacgtctca
++++++++++++++++++++++++++++++++++++++++++++++++++++++++    1650
cggacaaaattgctaatacggctattgatttgctttatttgcgattttgcagagt
```

FIG. 7D

```
gaaacgattttgagacgttttaataaaaaatcgcctagtgcttggattctcacca
++++++++++|++++++++++|++++++++++|++++++++++|++++++++++|++++++  1705
ctttgctaaaactctgcaaaattattttttagcggatcacgaacctaagagtggt
``` lambda t0 terminator

```
ataaaaaacgcccggcggcaaccgagcgttctgaacaaatccagatggagttctg
++++++++++|++++++++++|++++++++++|++++++++++|++++++++++|++++++  1760
tatttttgcgggccgccgttggctcgcaagacttgtttaggtctacctcaagac
``` lambda t0 terminator

```
aggtcattactggatctatcaacgggagtccaagcgagctcagccaatcgactgg
++++++++++|++++++++++|++++++++++|++++++++++|++++++++++|++++++  1815
tccagtaatgacctagatagttgccctcaggttcgctcgagtcggttagctgacc
``` lambda t0 terminator

```
cgagcggcatcttatttgccgactaccttggtgatctcgcctttcacgtagtgga
++++++++++|++++++++++|++++++++++|++++++++++|++++++++++|++++++  1870
gctcgccgtagaataaacggctgatggaaccactagagcggaaagtgcatcacct
                         260           255           250
                   * K G V V K T I E G K V Y H V
                   ◁\\\\\\\\\\ SmR \\\\\\\\\\\
```

```
caaattcttccaactgatctgcgcgcgaggccaagcgatcttcttcttgtccaag
++++++++++|++++++++++|++++++++++|++++++++++|++++++++++|++++++  1925
gtttaagaaggttgactagacgcgcgctccggttcgctagaagaagaacaggttc
        245           240           235
   F E E L Q D A R S A L R D E E Q G L
   ◁\\\\\\\\\\ SmR \\\\\\\\\\\
```

```
ataagcctgtctagcttcaagtatgacgggctgatactgggccggcaggcgctcc
++++++++++|++++++++++|++++++++++|++++++++++|++++++++++|++++++  1980
tattcggacagatcgaagttcatactgcccgactatgacccggccgtccgcgagg
        230           225           220           215
   Y A Q R A E L I V P Q Y Q A P L R E
   ◁\\\\\\\\\\ SmR \\\\\\\\\\\
```

```
attgcccagtcggcagcgacatccttcggcgcgattttgccggttactgcgctgt
++++++++++|++++++++++|++++++++++|++++++++++|++++++++++|++++++  2035
taacgggtcagccgtcgctgtaggaagccgcgctaaaacggccaatgacgcgaca
        210           205           200           195
   M A W D A A V D K P A I K G T V A S Y
   ◁\\\\\\\\\\ SmR \\\\\\\\\\\
```

FIG. 7E

```
accaaatgcgggacaacgtaagcactacatttcgctcatcgccagcccagtcggg
tggtttacgccctgttgcattcgtgatgtaaagcgagtagcggtcgggtcagccc
          190           185           180
  W  I  R  S  L  T  L  V  V  N  R  E  D  G  A  W  D  P
                         SmR
```
2090

```
cggcgagttccatagcgttaaggtttcatttagcgcctcaaatagatcctgttca
gccgctcaaggtatcgcaattccaaagtaaatcgcggagtttatctaggacaagt
     175           170           165           160
  P  S  N  W  L  T  L  T  E  N  L  A  E  F  L  D  Q  E
                         SmR
```
2145

```
ggaaccggatcaaagagttcctccgccgctggacctaccaaggcaacgctatgtt
ccttggcctagtttctcaaggaggcggcgacctggatggttccgttgcgatacaa
        155           150           145           140
  P  V  P  D  F  L  E  E  A  A  P  G  V  L  A  V  S  H  E
                         SmR
```
2200

```
ctcttgcttttgtcagcaagatagccagatcaatgtcgatcgtggctggctcgaa
gagaacgaaaacagtcgttctatcggtctagttacagctagcaccgaccgagctt
        135           130           125
  R  A  K  T  L  L  I  A  L  D  I  D  I  T  A  P  E  F
                         SmR
```
2255

```
gatacctgcaagaatgtcattgcgctgccattctccaaattgcagttcgcgctta
ctatggacgttcttacagtaacgcgacggtaagaggtttaacgtcaagcgcgaat
     120           115           110           105
  I  G  A  L  I  D  N  R  Q  W  E  G  F  Q  L  E  R  K
                         SmR
```
2310

```
gctggataacgccacggaatgatgtcgtcgtgcacaacaatggtgacttctacag
cgacctattgcggtgccttactacagcagcacgtgttgttaccactgaagatgtc
        100            95            90            85
  A  P  Y  R  W  P  I  I  D  D  H  V  V  L  T  V  E  V  A
                         SmR
```
2365

```
cgcggagaatctcgctctctccaggggaagccgaagtttccaaaaggtcgttgat
gcgcctcttagagcgagagaggtccccttcggcttcaaaggttttccagcaacta
           80            75            70
  R  L  I  E  S  E  G  P  S  A  S  T  E  L  L  D  N  I
                         SmR
```
2420

FIG. 7F

```
caaagctcgccgcgttgtttcatcaagccttacggtcaccgtaaccagcaaatca
++++++++++|++++++++++|++++++++++|++++++++++|++++++++++|++++++   2475
gtttcgagcggcgcaacaaagtagttcggaatgccagtggcattggtcgtttagt
         65         60         55         50
 L  A  R  R  T  T  E  D  L  R  V  T  V  T  V  L  L  D
<////////////////// SmR //////////////////| atatcactgtgtggcttcaggccgccatccactgcggagccgtacaaatgtacgg
++++++++++|++++++++++|++++++++++|++++++++++|++++++++++|++++++   2530
tatagtgacacaccgaagtccggcggtaggtgacgcctcggcatgtttacatgcc
         45         40         35         30
 I  D  S  H  P  K  L  G  G  D  V  A  S  G  Y  L  H  V  A
<////////////////// SmR //////////////////| ccagcaacgtcggttcgagatggcgctcgatgacgccaactacctctgatagttg
++++++++++|++++++++++|++++++++++|++++++++++|++++++++++|++++++   2585
ggtcgttgcagccaagctctaccgcgagctactgcggttgatggagactatcaac
         25         20         15
 L  L  T  P  E  L  H  R  E  I  V  G  V  V  E  S  L  Q
<////////////////// SmR //////////////////| agtcgatacttcggcgatcaccgcttccctcatgacattgcactccaccgctgat
++++++++++|++++++++++|++++++++++|++++++++++|++++++++++|++++++   2640
tcagctatgaagccgctagtggcgaagggagtactgtaacgtgaggtggcgacta
         10         5          1
 T  S  V  E  A  I  V  A  E  R  M
<////////////////// SmR //////////////////| gacatcagtcgatcatagcacgatcaacggcactgttgcaaatagtcggtggtga
++++++++++|++++++++++|++++++++++|++++++++++|++++++++++|++++++   2695
ctgtagtcagctagtatcgtgctagttgccgtgacaacgtttatcagccaccact taaacttatcatccccttttgctgatggagctgcacatgaactcgagtagggata
++++++++++|++++++++++|++++++++++|++++++++++|++++++++++|++++++   2750
atttgaatagtaggggaaaacgactacctcgacgtgtacttgagctcatccctat acagggtaatagatctaagcttctgcaggtcgactctagacggatccccctcaag
++++++++++|++++++++++|++++++++++|++++++++++|++++++++++|++++++   2805
tgtcccattatctagattcgaagacgtccagctgagatctgcctaggggagttc
                                                 tonB terminator tcaaaagcctccggtcggaggcttttgactttctgctatggaggtcaggtatgat
++++++++++|++++++++++|++++++++++|++++++++++|++++++++++|++++++   2860
agttttcggaggccagcctccgaaaactgaaagacgatacctccagtccatacta
       tonB terminator
```

FIG. 7G

```
tCTACAACCCCTGCGGATATAGCTTTTTTTCCAACTCATTGCGAGCGCGCTTCAG
++++++++++++++++++++++++++++++++++++++++++++++++++++++         2915
aGATCTTGGGGACGCCTATATCGAAAAAAAGGTTGAGTAACGCTCGCGCGAAGTC
         255        250        245        240
      L  G  Q  P  Y  L  K  K  E  L  E  N  R  A  R  K  L
                              tphR CGGTATCAAAAAAGTCTCCTTGAACTCACTCATGCTGAGTCTCTCTGCCCTAACT
++++++++++++++++++++++++++++++++++++++++++++++++++++++         2970
GCCATAGTTTTTTCAGAGGAACTTGAGTGAGTACGACTCAGAGAGACGGGATTGA
        235        230        225
   P  I  L  F  T  E  K  F  E  S  M  S  L  R  E  A  R  V
                              tphR GCAATGCTCATAGCAGCAATTGTGTTGCCTTGAGGGTCGCGCACTGGCGCTGCCA
++++++++++++++++++++++++++++++++++++++++++++++++++++++         3025
CGTTACGAGTATCGTCGTTAACACAACGGAACTCCCAGCGCGTGACCGCGACGGT
220        215        210        205
   A  I  S  M  A  A  I  T  N  G  Q  P  D  R  V  P  A  A  M
                              tphR TAGAGCGCACCCCCAGCTCCAGCTCTCCGTCGCTGCATGACCACCCTGATTGCCG
++++++++++++++++++++++++++++++++++++++++++++++++++++++         3080
ATCTCGCGTGGGGGTCGAGGTCGAGAGGCAGCGACGTACTGGTGGGACTAACGGC
        200        195        190        185
   S  R  V  G  L  E  L  E  G  D  S  C  W  G  S  Q  R
                              tphR GCAAGTTTCAAGCAGACCTAGCAGCTCCTCCAAGTCAGTCACCGTATGAGGGGTC
++++++++++++++++++++++++++++++++++++++++++++++++++++++         3135
CGTTCAAAGTTCGTCTGGATCGTCGAGGAGGTTCAGTCAGTGGCATACTCCCCAG
        180        175        170
   C  T  E  L  L  G  L  L  E  E  L  D  T  V  T  H  P  T
                              tphR AGTGCCACCCGCTCGATCATCTCTAGCCTTGCACGCGCCTCCTGTTGGGGGAGTC
++++++++++++++++++++++++++++++++++++++++++++++++++++++         3190
TCACGGTGGGCGAGCTAGTAGAGATCGGAACGTGCGCGGAGGACAACCCCCTCAG
165        160        155        150
   L  A  V  R  E  I  M  E  L  R  A  R  A  E  Q  Q  P  L  G
                              tphR CTGACAACAGCATCCGACCAATCGCAGAGCAGTACACCGGCAACCTAGATCCTAT
++++++++++++++++++++++++++++++++++++++++++++++++++++++         3245
GACTGTTGTCGTAGGCTGGTTAGCGTCTCGTCATGTGGCCGTTGGATCTAGGATA
        145        140        135        130
   S  L  L  M  R  G  I  A  S  C  Y  V  P  L  R  S  G  I
                              tphR
```

FIG. 7H

```
TCCTAGGCCCGTGCTCAAGCTGCGCCGTGCGGTCGAACGACCAATGATGATGGCA
AGGATCCGGGCACGAGTTCGACGCGGCACGCCAGCTTGCTGGTTACTACTACCGT        3300
          125            120            115
  G  L  G  T  S  L  S  R  R  A  T  S  R  G  I  I  I  A
  <tphR TCGTCCTCCAACAAAGTACCAAGCGAAGCGGATTCCCTGGTGCGCTCCGACAGTG
AGCAGGAGGTTGTTTCATGGTTCGCTTCGCCTAAGGGACCACGCGAGGCTGTCAC        3355
 110           105            100             95
  D  D  E  L  L  T  G  L  S  A  S  E  R  T  R  E  S  L  A
  <tphR CATCCAGTAGTGGCTGGGCCAATGCAGGCATGGGGCGCGATGACAGAAATGAATA
GTAGGTCATCACCGACCCGGTTACGTCCGTACCCCGCGCTACTGTCTTTACTTAT        3410
          90            85            80             75
  D  L  L  P  Q  A  L  A  P  M  P  R  S  S  L  F  S  Y
  <tphR GGCGATCAGCAGCGATTTGGGCTGCATCCAGAACAGTTTGCCGTCGCTCTCTAGA
CCGCTAGTCGTCGCTAAACCCGACGTAGGTCTTGTCAAACGGCAGCGAGAGATCT        3465
          70            65            60
  A  I  L  L  S  K  P  Q  M  W  F  L  K  G  D  S  E  L
  <tphR TAGCCAAGCTGTACCAGTGTGCTGAGCGAACGTCTGGCGGATGCTGGCGTGGACT
ATCGGTTCGACATGGTCACACGACTCGCTTGCAGACCGCCTACGACCGCACCTGA        3520
 55           50            45             40
  Y  G  L  Q  V  L  T  S  L  S  R  R  A  S  A  P  T  S  Q
  <tphR GCGTCAGCCTGGCTACCTCTGACAGCGTCAGCCGGGTATGCCGACGGTCAAAGCA
CGCACTCGGACCGATGGAGACTGTCGCAGTCGGCCCATACGGCTGCCAGTTTCGT        3575
  35           30            25             20
  T  L  R  A  V  E  S  L  T  L  R  T  H  R  R  D  F  C
  <tphR AGTCAGTACCCCCAATCCCTTGCGCAGCGATTCCACAAAGTTCTTGTCCTGCATA
TCAGTCATGGGGGTTAGGGAACGCGTCGCTAAGGTGTTTCAAGAACAGGACGTAT        3630
           15            10             5         1
  T  L  V  G  L  G  K  R  L  S  E  V  F  N  K  D  Q  M
  <tphR                                              tphR_tphC intergenic region
```

FIG. 7I

```
GTTCCATGGCCAACACTTGTCACTACTCTGACCTATGGTGTTCAATGCTTTTCCC
                                                                        3960
CAAGGTACCGGTTGTGAACAGTGATGAGACTGGATACCACAAGTTACGAAAAGGG
         60            65            70
 V  P  W  P  T  L  V  T  T  L  T  Y  G  V  Q  C  F  S
                        superfolder GFP GTTATCCGGATCACATGAAACGGCATGACTTTTTCAAGAGTGCCATGCCCGAAGG
                                                                        4015
CAATAGGCCTAGTGTACTTTGCCGTACTGAAAAAGTTCTCACGGTACGGGCTTCC
         75            80            85            90
 R  Y  P  D  H  M  K  R  H  D  F  F  K  S  A  M  P  E  G
                        superfolder GFP TTATGTACAGGAACGCACTATATCTTTCAAAGATGACGGGACCTACAAGACGCGT
                                                                        4070
AATACATGTCCTTGCGTGATATAGAAAGTTTCTACTGCCCTGGATGTTCTGCGCA
         95           100           105           110
 Y  V  Q  E  R  T  I  S  F  K  D  D  G  T  Y  K  T  R
                        superfolder GFP GCTGAAGTCAAGTTTGAAGGTGATACCCTTGTTAATCGTATCGAGTTAAAGGGTA
                                                                        4125
CGACTTCAGTTCAAACTTCCACTATGGGAACAATTAGCATAGCTCAATTTCCCAT
              115           120           125
 A  E  V  K  F  E  G  D  T  L  V  N  R  I  E  L  K  G
                        superfolder GFP TTGATTTTAAAGAAGATGGAAACATTCTTGGACACAAACTCGAGTACAACTTTAA
                                                                        4180
AACTAAAATTTCTTCTACCTTTGTAAGAACCTGTGTTTGAGCTCATGTTGAAATT
         130           135           140           145
 I  D  F  K  E  D  G  N  I  L  G  H  K  L  E  Y  N  F  N
                        superfolder GFP CTCACACAATGTATACATCACGGCAGACAAACAAAAGAATGGAATCAAAGCTAAC
                                                                        4235
GAGTGTGTTACATATGTAGTGCCGTCTGTTTGTTTTCTTACCTTAGTTTCGATTG
         150           155           160           165
 S  H  N  V  Y  I  T  A  D  K  Q  K  N  G  I  K  A  N
                        superfolder GFP TTCAAAATTCGCCACAACGTTGAAGATGGTTCCGTTCAACTAGCAGACCATTATC
                                                                        4290
AAGTTTTAAGCGGTGTTGCAACTTCTACCAAGGCAAGTTGATCGTCTGGTAATAG
              170           175           180
 F  K  I  R  H  N  V  E  D  G  S  V  Q  L  A  D  H  Y
                        superfolder GFP
```

FIG. 7K

```
AACAAAATACTCCAATTGGCGATGGCCCTGTCCTTTTACCAGACAACCATTACCT
TTGTTTTATGAGGTTAACCGCTACCGGGACAGGAAAATGGTCTGTTGGTAATGGA
    185         190         195         200
 Q  Q  N  T  P  I  G  D  G  P  V  L  L  P  D  N  H  Y  L
```
                                                                4345
```
                          superfolder GFP GTCGACACAATCTGTCCTTTCGAAAGATCCCAACGAAAAGCGTGACCACATGGTC
CAGCTGTGTTAGACAGGAAAGCTTTCTAGGGTTGCTTTTCGCACTGGTGTACCAG
    205         210         215         220
 S  T  Q  S  V  L  S  K  D  P  N  E  K  R  D  H  M  V
```
                                                                4400
```
                          superfolder GFP CTTCTTGAGTTTGTAACTGCTGCTGGGATTACACATGGCATGGATGAGCTCTACA
GAAGAACTCAAACATTGACGACGACCCTAATGTGTACCGTACCTACTCGAGATGT
    225         230         235
 L  L  E  F  V  T  A  A  G  I  T  H  G  M  D  E  L  Y
```
                                                                4455
```
                          superfolder GFP AAGGTGGCGGTTCTGAATTCACACCTAGGTAAactag      3'
TTCCACCGCCAAGACTTAAGTGTGGATCCATTtgatc      5'      ...    4492

K  G  G  G  S  E  F  T  P  R  ■
 ▷ ------(in frame with superfolder GFP)----▶
superfolder GFP
```

FIG. 7L

TEREPHTHALATE BIOSENSORS AND USES THEREOF

CROSS REFERENCE TO RELATED APPLICATION

This claims the benefit of U.S. Provisional Application No. 62/972,365, filed Feb. 10, 2020, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

REFERENCE TO A SEQUENCE LISTING

The Sequence Listing written in file 573185SEQLST.txt is 25,221 bytes, was created on Sep. 10, 2023, and is hereby incorporated by reference.

FIELD

This disclosure relates to biosynthesis of compounds in prokaryotic organisms, in particular biosensors for terephthalate and methods of their use.

BACKGROUND

Terephthalic acid (TPA) is an important commodity chemical with an estimated global demand of >30 million tonnes. Currently it is synthesized from petroleum sources using heterogeneous catalysts. Once TPA is made and used for polyethylene terephthalate (PET) bottles, the polymer is highly recalcitrant to degradation. Microbial synthesis of TPA has been envisioned but the process lacks sufficient efficiency and productivity to be economically feasible. Similarly, PET degradation using biocatalysts has been shown, but the enzymes are early in their evolution and lack optimal efficiency.

SUMMARY

A key component and bottleneck in biosynthesis of TPA or recycling of PET, is establishment of a high throughput screening platform. The present disclosure establishes a sensor-reporter system for TPA. When the sensor is established in a microorganism system (e.g., *Acinetobacter baylyi* ADP1), it allows detection of TPA transport in the cell and can be used for detection of TPA as a synthesis or degradation product. The sensor makes it possible to engineer high efficiency biocatalysts that can facilitate TPA formation as a synthetic or a degradation product.

In some embodiments, a TPA biosensor is provided. In some embodiments, the biosensor includes a nucleic acid encoding a TphR protein, a TphR-regulated promoter comprising the nucleic acid sequence of nucleotides 4-115 of SEQ ID NO: 11 or nucleotides 4-114 of SEQ ID NO: 12, and a nucleic acid encoding a reporter protein operably linked to the promoter. In some examples, the reporter protein is a fluorescent protein (such as a green fluorescent protein).

In some embodiments, the TPA biosensor includes a nucleic acid sequence with at least 95% sequence identity to nucleotides 2862-4457 of SEQ ID NO: 1 or the reverse complement thereof. In particular examples, the TPA biosensor includes or consists of the nucleic acid sequence of nucleotides 2862-4457 of SEQ ID NO: 1 or the reverse complement thereof.

Vectors including the TPA biosensor nucleic acid are also provided. In some embodiments, the vector includes a nucleic acid sequence with at least 95% sequence identity to nucleotides 2862-4457 of SEQ ID NO: 1 or the reverse complement thereof. In some examples, the vector includes a nucleic acid including or consisting of the nucleic acid sequence of nucleotides 2862-4457 of SEQ ID NO: 1 or the reverse complement thereof. In other examples, the vector includes or consists of the nucleic acid sequence of SEQ ID NO: 1 or SEQ ID NO: 2.

Also provided are host cells including the TPA biosensor nucleic acid or vectors disclosed herein. In some examples, the host cell is a bacterial cell. In one non-limiting example, the host cell is an *Acinetobacter baylyi* cell (such as *A. baylyi* ADP1).

Methods of detecting TPA with the disclosed biosensors are also provided. In some embodiments, the methods include culturing a host cell including a TPA biosensor nucleic acid under conditions sufficient to detect TPA (such as conditions sufficient to produce TPA) and detecting output from the reporter protein. In some examples, the reporter protein is a fluorescent protein, and detecting the output is by detecting fluorescent signal (for example, using flow cytometry). In some examples, the TPA is produced by the cell. The host cell may also express one or more enzymes that are involved in production of TPA (such as a heterologous or modified enzyme). In other examples, the TPA is produced outside of the cell (for example, in the environment of the cell). In some examples, the TPA is produced outside the cell, for example, by degradation of PET. The host cell may also express a transporter capable of transporting TPA into the host cell (such as a heterologous or modified transporter).

The foregoing and other features of the disclosure will become more apparent from the following detailed description, which proceeds with reference to the accompanying figures.

BRIEF DESCRIPTION OF THE DRAWINGS

FIG. 1A is a schematic diagram of the general strategy for high throughput screening and detection of metabolite (e.g., TPA) by detecting fluorescent signal, such as using flow cytometry. FIG. 1B is a vector map of an exemplary TPA biosensor plasmid. FIG. 1C is a diagram showing the sequence of a portion of the tphR encoding region, intergenic region, and a portion of the superfolder GFP encoding region of the plasmid (nucleic acids 3501-3780 of the plasmid, of SEQ ID NO: 13, and its reverse complement (SEQ ID NO:14) and amino acids 1-43 of SEQ ID NO: 4 and amino acids 1-13 of SEQ ID NO: 3). Amino acid sequence MQDKNFVESLRKGLGVLTCFDRRHTRLTLSEVARLTQSTPASA in FIG. 1C is amino acids 1-43 of SEQ ID NO:4. Amino acid sequence MASKGEELFTGVV in FIG. 1C is amino acids 1-13 of SEQ ID NO:3. Nucleotide sequence labeled tphR_promo_lib3a_f (oRJ151) is SEQ ID NO:17. Nucleotide sequence labeled SDseq_sfGFP_fwd(oRJ012) is SEQ ID NO:18. Nucleotide sequence labeled tphR_promo_10_lib3b_f (oRJ153) is SEQ ID NO:15.

FIG. 2A shows the sequence of the diversified regions of the promoter $Pt_ph$ in three generations of the sensor (SEQ ID NOs: 10-12). pTPA1 is SEQ ID NO:10. pTPA2 is SEQ ID NO:11. pTPA3 is SEQ ID NO:12. The performance of the three generations is shown in FIG. 2B. FIG. 2C shows specificity of pTPA3 sensor for TPA.

FIGS. 7A-7L show the nucleic acid sequence of plasmid pTPA3 (SEQ ID NOs: 1 and 2) and amino acid sequences of the encoded proteins (SEQ ID NOs: 3-9). Amino acid sequence of repA in FIGS. 7A-7C is SEQ ID NO:9. Amino acid sequence of Hypothetical protein in FIG. 7C is SEQ ID NO:8. Amino acid sequence of Hypothetical protein starting in FIG. 7D and ending in FIG. 7C is SEQ ID NO:7. Amino acid sequence labeled Factor Xa site and in frame with Factor Xa site in FIG. 7D is SEQ ID NO:6. Amino acid sequence of SmR in FIGS. 7E-7G is SEQ ID NO:5. Amino acid sequence of tphR in FIGS. 7H-7I is SEQ ID NO:4. Amino acid sequence of superfolder GFP in FIGS. 7J-7L is SEQ ID NO:3. Amino acid sequence labeled "(in frame with superfolder GFP)" in FIG. 7L is SEQ ID NO:16.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NOs: 1 and 2 are the nucleic acid sequences of plasmid pTPA3 (complementary strands).

SEQ ID NO: 3 is the amino acid sequence of a superfolder GFP (sfGFP).

SEQ ID NO: 4 is the amino acid sequence of TphR.

SEQ ID NO: 5 is the amino acid sequence of SmR.

SEQ ID NO: 6 is the amino acid of a Factor Xa site and in frame sequence.

SEQ ID NOs: 7 and 8 are the amino acid sequence of two hypothetical proteins.

SEQ ID NO: 9 is the amino acid sequence of repA.

SEQ ID NOs: 10-12 are nucleic acid sequences of the promoter region of three generations of TPA sensors. pTPA1 is SEQ ID NO:10. pTPA2 is SEQ ID NO:11. pTPA3 is SEQ ID NO:12.

Figure 1A:
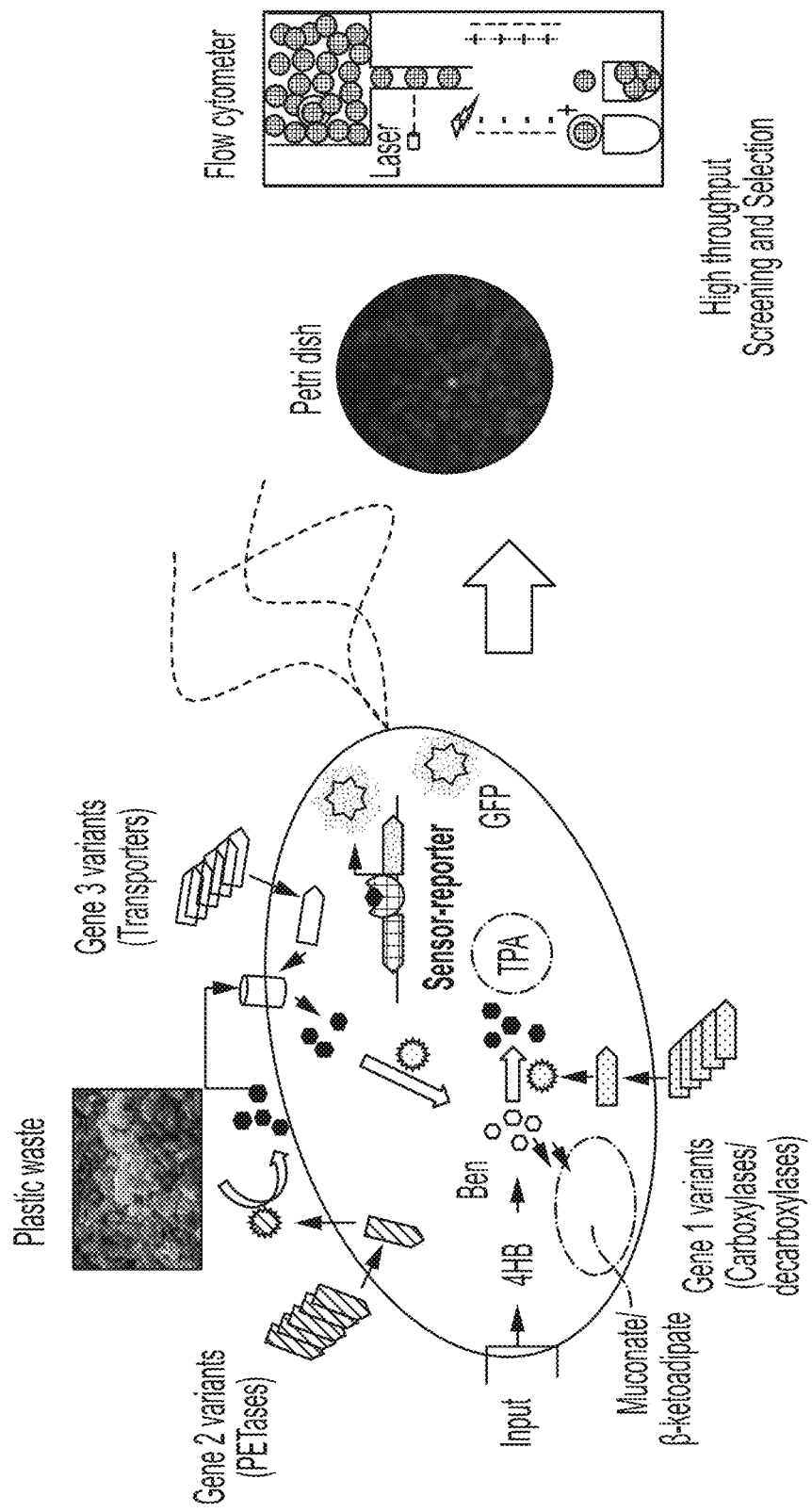
FIGS. 1A-1C show TPA biosensor.
Figure 1B:
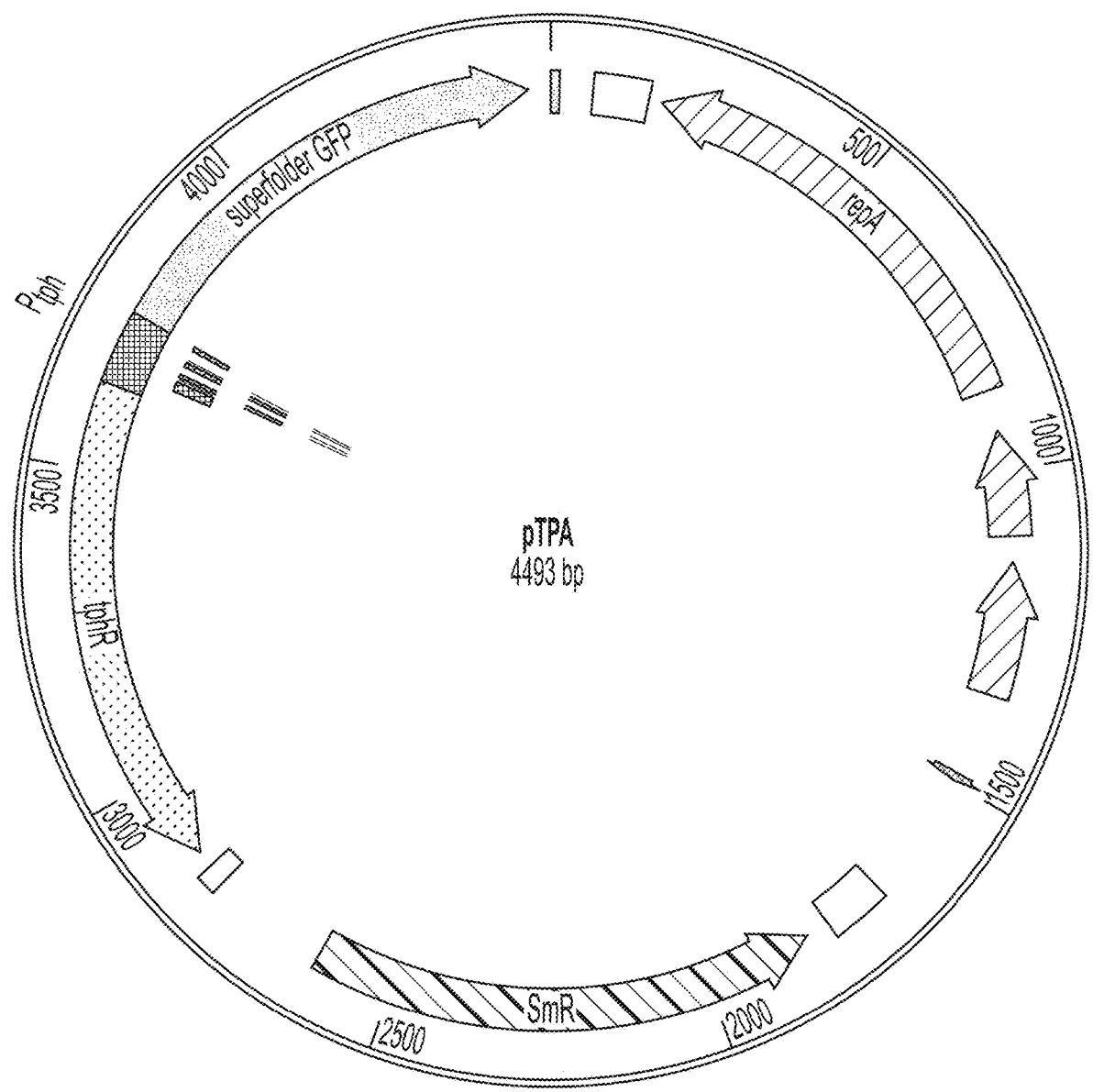
Figure 1C:
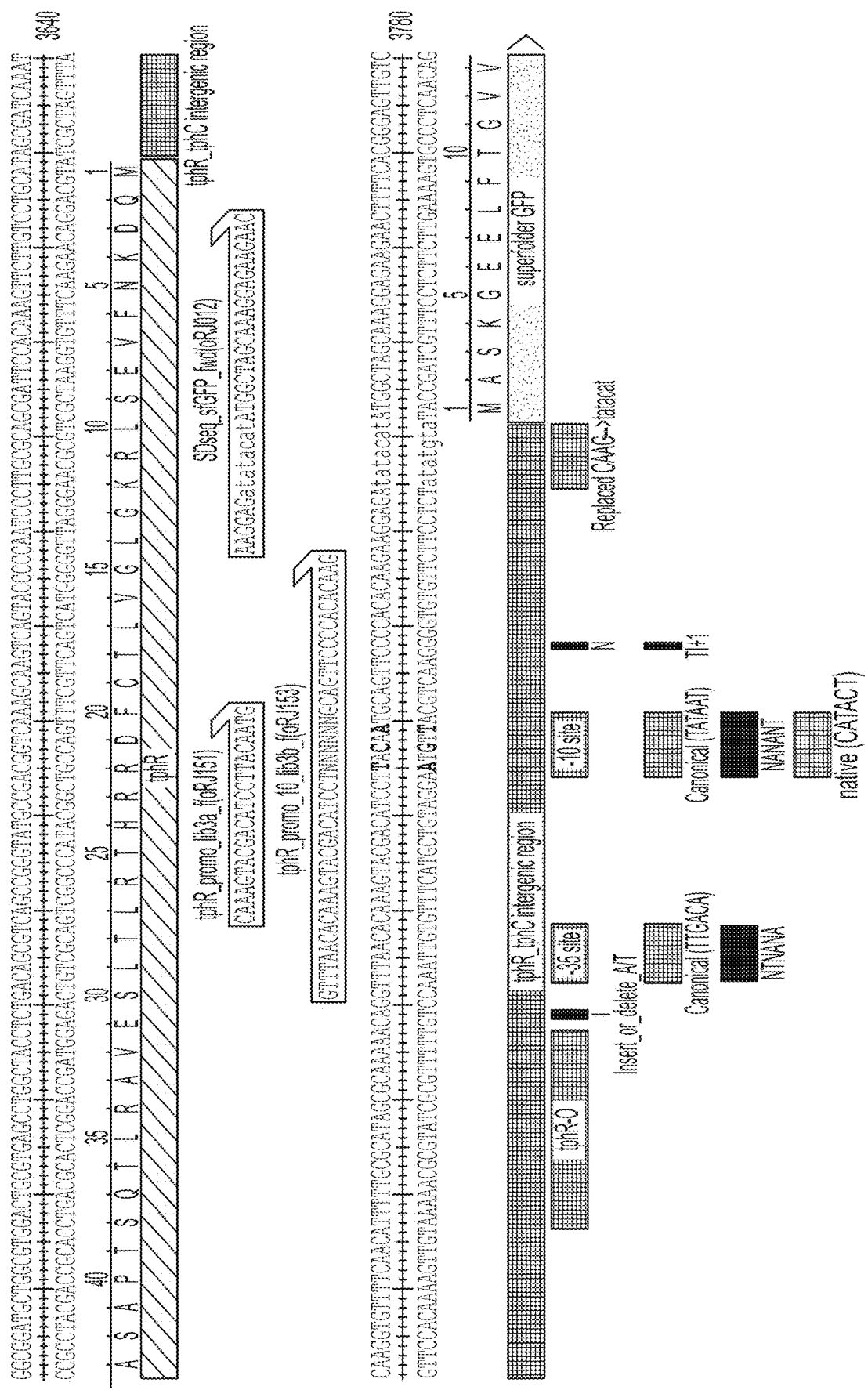

SEQ ID NOs:13-14 are nucleotide sequences of a portion of an exemplary TPA biosensor plasmid (complementary strands) (FIG. 1C).

SEQ ID NO:15 is nucleotide sequence of tphR_promo_10_lib3b_f (oRJ153) (FIG. 1C).

Figure 7J:
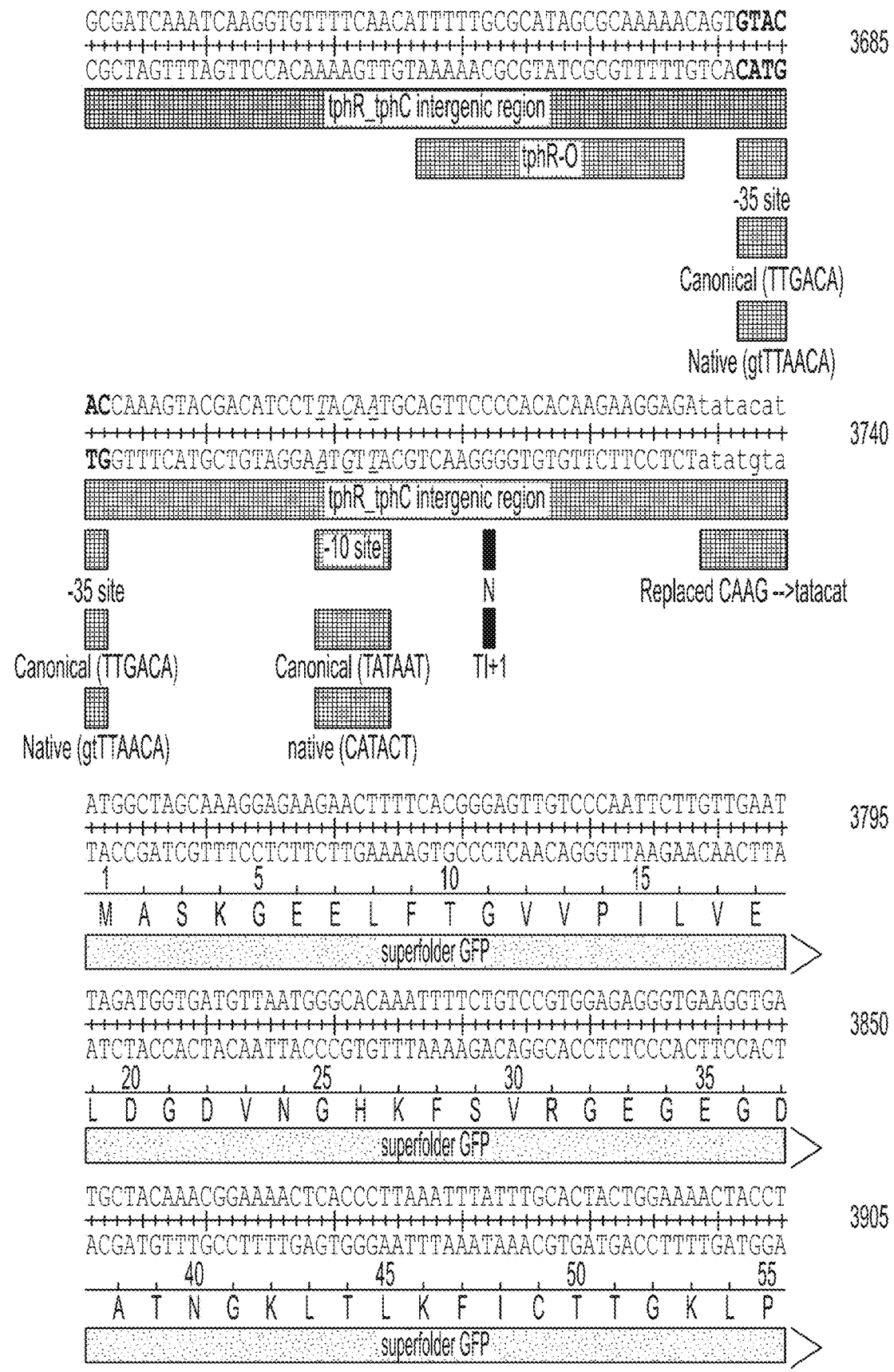

SEQ ID NO:16 is an amino acid sequence in frame with superfolder GFP (FIG. 7L).

SEQ ID NO:17 is nucleotide sequence of tphR_promo_lib3a_f(oRJ151) (FIG. 1C).

SEQ ID NO: 18 is nucleotide sequence of SDseq_sfGFP_fwd(oRJ012) (FIG. 1C).

DETAILED DESCRIPTION

*A. baylyi* ADP1 can be used as a platform organism. Advantages of ADP1 include that it is naturally competent, it has an exceptionally high frequency of natural transformation and recombination, it is easy to alter the chromosome, and readily uptakes plasmids and DNA from the medium. In addition, ADP1 grows quickly (aerobically) and has metabolic capabilities that differ from other model organisms. Further, whole genome resequencing allows facile identification of chromosomal mutations. The disclosure also utilizes Evolution by Amplification and Synthetic biology (EASy; Tumen-Velasquez et al., *Proc. Natl. Acad. Sci.* 115:7105-7110, 2018). Increased gene dosage allows evolution of genes that do not enable growth in single copy. EASy can be combined with diversified DNA libraries.

For a circular plastics economy, it is important to be able to synthesize molecules of interest from renewable sources and be able to degrade them at will. Synthetic biology is a viable route for such synthesis and degradation of anthropogenic molecules. For any biotransformation to be economically sustainable, an initial step is establishment of an efficient microbial system, which acts as micro-factories performing the biotransformation. The overall efficiency of such biotransformation lies in the ability to transport TPA into the microbial factories (e.g., for degradation and "upcycling") and ability to perform biotransformation at a very high catalytic rate for synthesis from renewable feedstocks or as a degradation product from plastic wastes. The natural pool of transporters and biocatalysts typically lack sufficient efficiency to make this whole process economically feasible. However, these proteins can be evolved in silico and tested in the laboratory, and a screening method with a very high throughput is needed. A sensor-reporter technology, that can 'sense' TPA and 'report' by expressing a detectable marker (e.g., a fluorescent protein), which can be conveniently visualized or estimated and used for high throughput is provided herein.

The TPA sensors provided herein allow detection of very low quantities of TPA inside the cell. If the enzymatic activity under consideration is very weak, it will not accumulate substantial amounts of TPA, even when the number of copies has been amplified. At substantially low quantities, TPA might not support growth, hence any beneficial mutation which accumulates during amplification and de-amplification will be lost. But in the presence of a specific and sensitive sensor, such as those provided herein, even very small quantities of TPA can be detected and reported as fluorescence signal. If the gene of interest is amplified, it will produce higher quantities of the product. If a beneficial mutation is added in the gene, there will be a correlated increase in the product. Any increase in intracellular concentration of product will be reported as increase in fluorescence signal, which can be conveniently measured and screened, for example, on a petri dish, or sorted using a flow cytometer.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of*

*Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. All database accession numbers (such as GenBank or UniProt accession numbers) are incorporated herein by reference in their entirety, as present in the database on Feb. 10, 2021. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Biosensor: A biological molecule (such as a nucleic acid, peptide, or protein) that can detect a change in environment, for example, in a dose-dependent manner. In some examples, a biosensor includes a protein (such as a transcription factor) that can sense a change in concentration of a small molecule in or around a cell. The biosensor may be coupled (directly or indirectly) to a reporter, including but not limited to an antibiotic resistance gene, a gene encoding a fluorescent protein (such as a green fluorescent protein), or a metabolic gene (such as lacZ). The reporter then indicates the presence and/or amount of the detected molecule, for example, by antibiotic resistance, fluorescence, or color change.

Heterologous: Originating from a different genetic source or species. A gene that is heterologous to a prokaryotic cell originates from an organism or species other than the prokaryotic cell in which it is expressed. Methods for introducing a heterologous gene in a cell or organism are well known in the art, for example transformation with a nucleic acid, including electroporation, lipofection, particle gun acceleration, and homologous recombination.

Isolated: An "isolated" biological component (such as a nucleic acid molecule, protein, or cell) has been substantially separated or purified away from other biological components in the cell of the organism, or the organism itself, in which the component occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

It is understood that the term "isolated" does not imply that the component is free of trace contamination, and can include molecules that are at least 50% isolated, such as at least 50%, 55%, 60%, 65%, 70%, 75%, 80%, 85%, 90%, 95%, 98%, 99%, or even 100% isolated.

Modified: A "modified" nucleic acid or polypeptide is one that has a sequence that is not naturally occurring or has a sequence that is made by an artificial combination of two or more otherwise separated segments of sequence. A modified nucleic acid or polypeptide is often produced by chemical synthesis or, more commonly, by the artificial manipulation of isolated segments of nucleic acids, e.g., by genetic engineering techniques.

Operably linked: A first nucleic acid is operably linked with a second nucleic acid when the first nucleic acid is placed in a functional relationship with the second nucleic acid. For instance, a regulatory region is operably linked to a coding sequence if the regulatory region affects the transcription or expression of the coding sequence. Generally, operably linked DNA sequences are contiguous and, where necessary to join two protein-coding regions, in the same reading frame.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element.

Recombinant: A nucleic acid or protein that is not naturally occurring or has a sequence that is made by an artificial combination of two otherwise separated segments of nucleotides or amino acids. This artificial combination is often accomplished by chemical synthesis or, more commonly, by the artificial manipulation of isolated segments of nucleic acids, e.g., by genetic engineering techniques known to those of skill in the art. The term recombinant includes nucleic acids or proteins that have been altered solely by addition, substitution, or deletion of a portion of the nucleic acid sequence or amino acid sequence, respectively.

Terephthalic acid (TPA): A commodity chemical and polymer precursor with the structure:

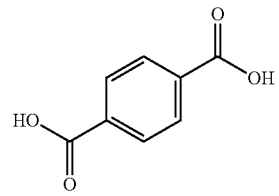 [SMILES: O=C(O)c1ccc(C(=O)O)cc1]

TphR: A transcription factor belonging to the IclR family from Comamonas genus. TphR binds to terephthalic acid (TPA) to express downstream genes involved in transport of TPA into the cell. GenBank reference sequence WP_012837656.1 is an exemplary amino acid sequence of TphR.

Transduced and Transformed: A vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule is introduced into such a cell, including transformation with plasmid vectors, and introduction of naked DNA by electroporation, lipofection, and particle gun acceleration.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and gram positive bacterial cells. Exemplary vectors include those for use in *E. coli*, *P. putida*, and *A. baylyi*.

II. TPA Biosensors

Disclosed herein are biosensors for TPA. In some embodiments, the biosensors include a nucleic acid encoding a TphR protein, a promoter regulated by TPA, and a reporter that is operably linked to the promoter. In particular embodiments, the promoter includes one or more modifications from the naturally occurring promoter, for example, to improve sensitivity and/or specificity of response to TPA. In some examples, the TphR is a *Comamonas testosteroni* TphR protein (such as SEQ ID NO: 4). The reporter encodes a protein that generates a detectable output, such as an antibiotic resistance gene, a fluorescent protein-encoding gene, or a metabolic gene. In some examples, the reporter encodes a fluorescent protein, such as a green fluorescent protein (GFP). In one non-limiting example, the reporter encodes a superfolder GFP (sfGFP). Other GFPs or related fluorescent proteins (such as eGFP, red fluorescent protein (RFP), superfolder RFP (sfRFP), mCherry, sfCherry, mStrawberry, mOrange, or dTomato) can also be used as a reporter in the biosensors.

In some examples, the promoter region of the biosensor includes the nucleic acid sequence of nucleotides 4-115 of SEQ ID NO: 11 or nucleotides 4-114 of SEQ ID NO: 12. In other examples, the biosensor includes a nucleic acid sequence with at least 90% sequence identity (such as 91%, 92%, 93%, 94%, 95%, 96%, 97%, 98%, 99%, or 100% identity) to the nucleic acid sequence of nucleotides 2862-4457 of SEQ ID NO: 1 or the reverse complement thereof. In further examples, the biosensor includes or consists of the nucleic acid sequence of nucleotides 2862-4457 of SEQ ID NO: 1 or the reverse complement thereof.

Nucleic acid molecules of the TPA biosensors disclosed herein include recombinant nucleic acids which are incorporated into a vector, into an autonomously replicating plasmid or virus, or into the genomic DNA of a host cell, or which exists as a separate molecule independent of other sequences.

In some examples, the vector includes a sequence with at least 90% identity (such as 91%, 92%, 93%, 94%, 95%, 96%, 97%, 98%, 99%, or 100% identity) to the nucleic acid sequence of nucleotides 2862-4457 of SEQ ID NO: 1 or the reverse complement thereof. In other examples, the vector includes a nucleic acid sequence including or consisting of nucleotides 2862-4457 of SEQ ID NO: 1 or the reverse complement thereof.

In some non-limiting examples, the vector includes one or more of an origin of replication, a nucleic acid encoding a replication initiator protein (such as RepA), a nucleic acid encoding an antibiotic resistance gene (such as SmR), or other features. In one non-limiting example, the vector includes or consists of the nucleic acid sequence of SEQ ID NO: 1 or SEQ ID NO: 2. One of ordinary skill in the art will recognize that portions of the vectors can be altered (for example, modified or replaced) with other appropriate components. For example, the proteins referred to as "hypothetical proteins" in the vector shown in FIG. 1B can be replaced with other elements providing desired activity, as can the other protein coding regions in the vector.

Vectors for cloning, replication, and/or expression of the disclosed nucleic acid molecules include bacterial plasmids, such as bacterial cloning or expression plasmids.

Exemplary bacterial plasmids into which the nucleic acids can be cloned include *E. coli* plasmids, such as pBR322, pUC plasmids (such as pUC18 or pUC19), pBluescript, pACYC184, pCD1, pGEM® plasmids (such as pGEM®-3, pGEM®-4, pGEM-T® plasmids; Promega, Madison, WI), TA-cloning vectors, such as pCR® plasmids (for example, pCR® II, pCR® 2.1, or pCR® 4 plasmids; Life Technologies, Grand Island, NY) or pcDNA plasmids (for example pcDNA™3.1 or pcDNA™3.3 plasmids; Life Technologies). In some examples, the vector includes a heterologous promoter which allows protein expression in bacteria. Exemplary vectors include pET vectors (for example, pET-21b), pDEST™ vectors (Life Technologies), pRSET vectors (Life Technologies), pBAD vectors, and pQE vectors (Qiagen). The disclosed nucleic acids can also be cloned into *B. subtilis* plasmids, for example, pTA1060 and pHT plasmids (such as pHT01, pHT43, or pHT315 plasmids). In some examples, the vector is a broad host range vector, such as pBTBX vectors (Prior et al., *Biotechnol. Bioeng.* 106:326-332, 2010), pBTL vectors (Lynch et al., *Biotechnol. Bioeng.* 94:151-158, 2006), or BAV1K vectors (Murin et al., *Appl. Env. Microbiol.* 78:280-283, 2012). In non-limiting examples, the vector is based on vector pBTL-2 (Addgene plasmid #22806) or vector pBAV1K-PT5-gfp (Addgene plasmid #26702)

Also provided are host cells including a nucleic acid including one or more of the disclosed TPA biosensors or vectors including the nucleic acid sequence of one or more of the disclosed TPA biosensors. In some embodiments, the cells are bacterial cells. Bacterial cells are available from numerous sources, including commercial sources known to those skilled in the art, such as the American Type Culture Collection (ATCC; Manassas, VA). Commercial sources of cells used for recombinant protein expression also provide instructions for usage of such cells. Suitable bacteria for use in the methods disclosed herein include but are not limited to *Pseudomonas* (e.g., *P. putida*), *Escherichia* (e.g., *E. coli*), *Acinetobacter* (e.g., *Acinetobacter baylyi*), and *Rhodococcus*. In particular non-limiting examples, the bacterial cells are *A. baylyi* cells, such as *A. baylyi* ADP1.

In some examples, the TPA biosensor nucleic acid or vector including the TPA biosensor nucleic acid is introduced extrachromosomally and replicated within the host cell. In other examples, after introduction of the plasmid, a double homologous recombination event occurs and the one or more genes are inserted into the genome of the host cell.

Transformation of a bacterial cell with recombinant DNA can be carried out by techniques known to those skilled in the art. Where the host is bacterial, competent cells which are capable of DNA uptake can be prepared from cells harvested after exponential growth phase and subsequently treated by the CaCl$_2$) method using procedures well known in the art. Alternatively, MgCl$_2$ or RbCl can be used. Bacteria can also be transformed by electroporation, conjugation, or transduction.

III. Methods of Use

Also disclosed herein are methods of utilizing the TPA biosensors. In some embodiments, the methods include detecting production of TPA in a sample. In other embodiments, the methods include detecting presence of TPA in the environment of a cell, for example, produced by degradation of a compound, such as PET. In further embodiments, the methods include detecting TPA transport into a cell.

In some examples, the methods can be used to detect or identify improved or increased production of TPA by the cell and/or improved or increased transport of TPA into the cell. For example, as shown in FIG. 1A, cells including the TPA biosensor can be transformed with one or more variants (such as a library of variants) of one or more of the enzymes involved in production of TPA and can be screened for increased production of TPA, to identify variants with desirable properties. Exemplary enzymes involved in production of TPA include 3-deoxy-D-arabinonoheptulosonate 7-phosphate (DAHP) synthases, chorismite pyruvate-lyase (UbiC), feruloyl-CoA synthetase (Fcs), enoyl-CoA hydratase/aldolase (Ech), vanillin dehydrogenase (Vdh), prephenate dehydratase (PHA2), and phenolic acid decarboxylase (BsdBCD).

Alternatively, or in addition, as also illustrated in FIG. 1A, cells including the TPA biosensor can be transformed with one or more variants (such as a library of variants) of one or more transporters that can transport TPA into the cell and can be screened for increased TPA in the cell, to identify variants with desirable properties. Exemplary transporters that can transport TPA into bacterial cells include MFS transporters for di- or tri-carboxylic acids such as MucK, CitP or GudP.

In some examples, bacterial cells (e.g., *A. baylyi*) are transformed with a plasmid encoding a disclosed biosensor. In other examples, the cells are transformed with variants of the biosensor (such as a library encoding variants of the biosensor). The cells are screened for presence and/or amount of TPA by detecting output of the reporter, such as fluorescence. In some examples, cells including a disclosed biosensor are cultured under conditions sufficient for detection of TPA or production of TPA and output of the reporter is detected. In one example, the reporter is a fluorescent protein (such as a GFP, for example, sfGFP), and fluorescence is detected.

Samples can be screened for production of or presence of TPA via either flow cytometry (Jha et al., *Nucl. Acids Res.* 42:8150-8160, 2014) or on a solid growth media (e.g., petri dish; Jha et al., *ACS Syn. Biol.* 9:1234-1239, 2020) and selection based on the fluorescence of the individual cell (for flow cytometry) or fluorescence (or other visually detectable signal) of the colonies on a solid growth media. If the reporter gene in the sensor plasmid is a survival enhancing gene (for example the protein product of the gene provides resistance to a suitable antibiotic or the protein product of the gene provides a suitable nutrient to the auxotroph), the screening can be carried out based on growth characteristics, such as the growth rate.

EXAMPLES

The following examples are provided to illustrate certain particular features and/or embodiments. These examples should not be construed to limit the disclosure to the particular features or embodiments described.

Example 1

Generation of TPA Biosensor

A TPA biosensor was constructed using TPA responsive transcription factor from *Comamonas testosteroni*. The transcription factor, tphR, activates the expression of reporter, sfGFP upon binding to TPA molecule. The promoter P$_{tph}$, was diversified in the regions of −10, −35, and transcription initiation region. The plasmid library consisting of diversification in the promoter region was then transformed in different *A. baylyi* ADP1 strains and sorted for high GFP fluorescence using flow cytometry.

Figures 2A, 2B, 2C:
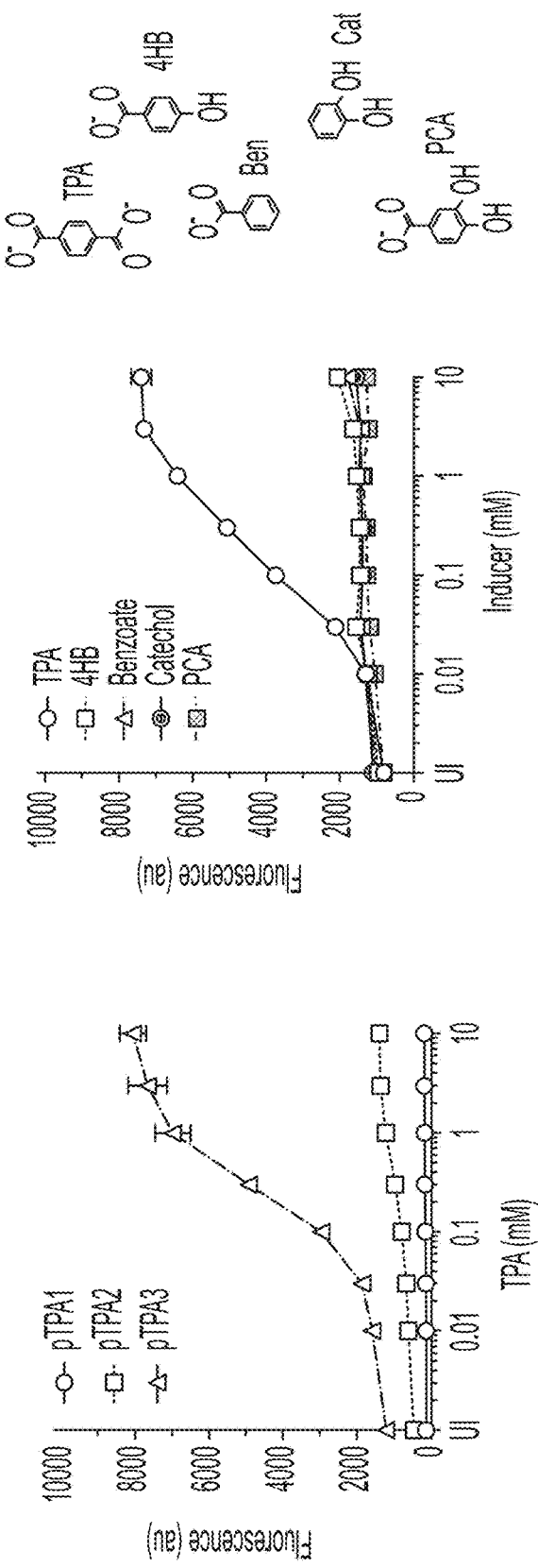
FIGS. 2A-2C show optimization of a TPA biosensor.

Three generations of TPA sensor, pTPA1 (native promoter, SEQ ID NO:10), pTPA2 (mutations only in −10 site, SEQ ID NO:11) and pTPA3 (mutations in both −10 and −35 sites SEQ ID NO:12) (FIG. 2A) showed different levels of activity in ADP1 (FIG. 2B). Similarly, activity levels varied in different ADP1 strains. pTPA3 sensor was further tested for specificity. Several aromatic molecules were dosed in the concentration range of 0-10 mM and fluorescence response recorded. The pTPA3 sensor showed high specificity for TPA molecule (FIG. 2C).

Example 2

Characterization of TPA3 Biosensor

Figure 3:
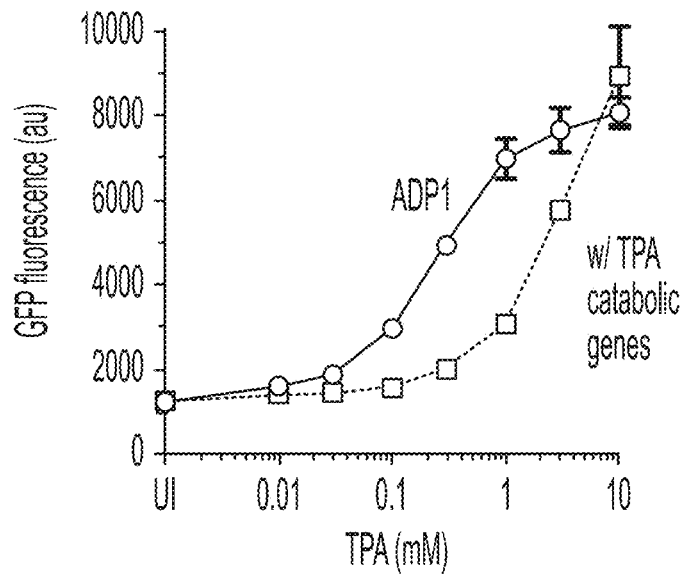
FIG. 3 is a graph showing TPA production in ADP1 strains with and without TPA catabolic genes.

ADP1 strains with TPA catabolic genes will decrease the intracellular pool of TPA. The TPA sensor (pTPA3) was sensitive to such changes and showed lower fluorescence response especially at low extracellular TPA concentration (FIG. 3).

Figure 4:
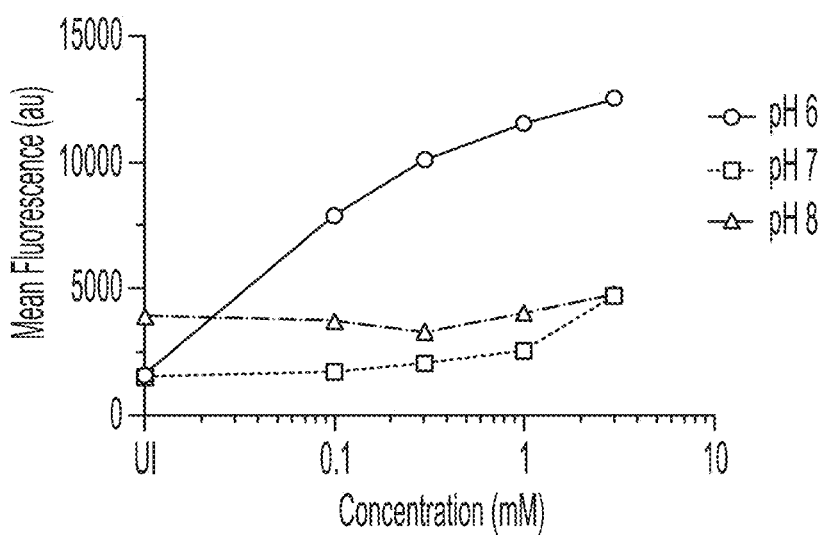
FIG. 4 is a graph showing improved TPA transport in ADP1 at acidic pH.

TPA is expected to be better transported at acidic pH than at neutral or basic pH. The TPA sensor was able to detect this improvement in TPA transport at acidic pH and showed higher fluorescence response, possibly due to higher intracellular pool of the molecule. ADP1 strain with native transporter (mucK) was grown and induced with TPA at different concentrations. Though experiments shown FIG. 2 and FIG. 3 were conducted at pH 7 and high response of the sensor was observed, in this experiment high concentration of bicarbonate (30 mM) showed diminished sensor response at pH 7 (FIG. 4). While working at different pH, high response of the pTPA3 sensor was observed at pH 6, and this suggests that pH 6 facilitates better transport at acidic pH and hence, intracellular pool of TPA would increase, with an increased response from TPA sensor.

Figure 5:
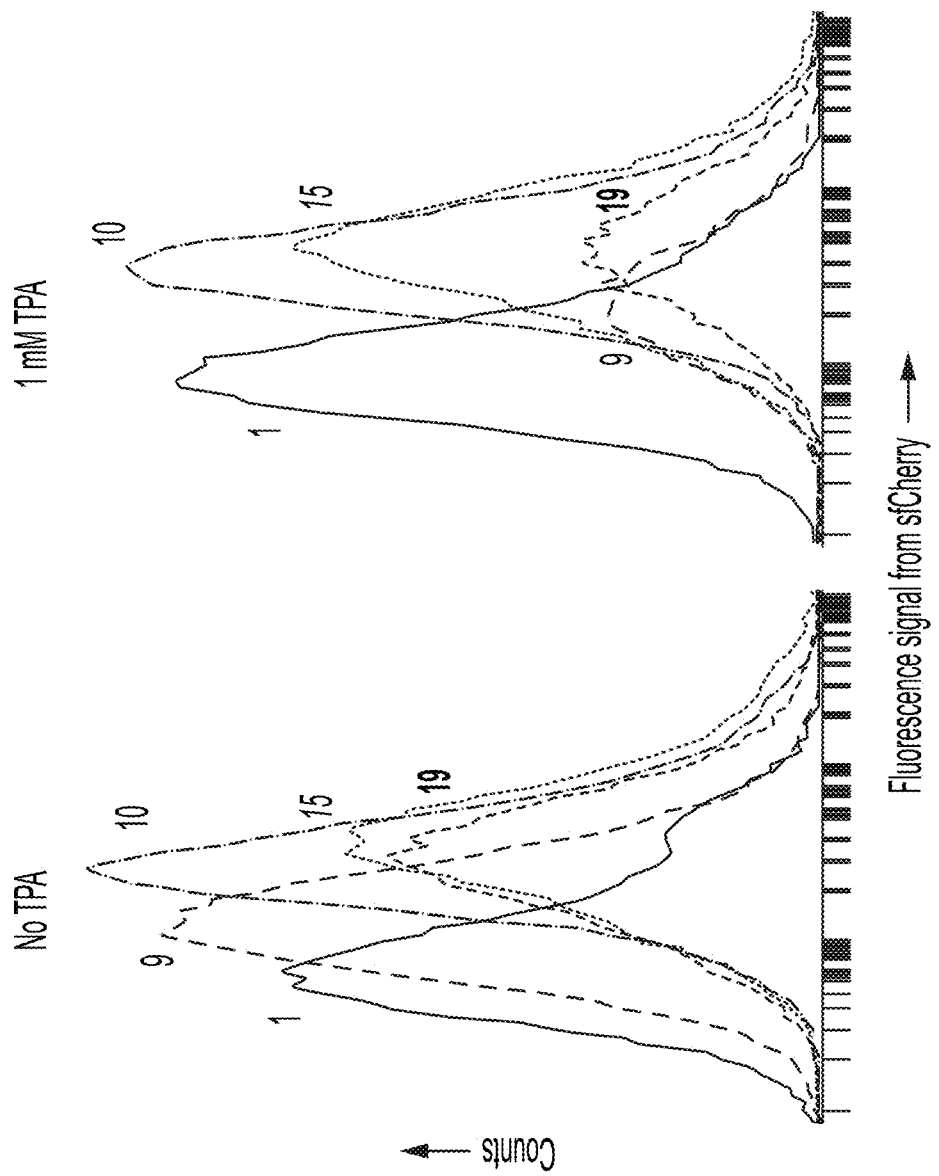
FIG. 5 shows signal from cells including pTPA3 and varying copy number of sfCherry in the presence of TPA (left) or 1 mM TPA (right).
Figure 6:
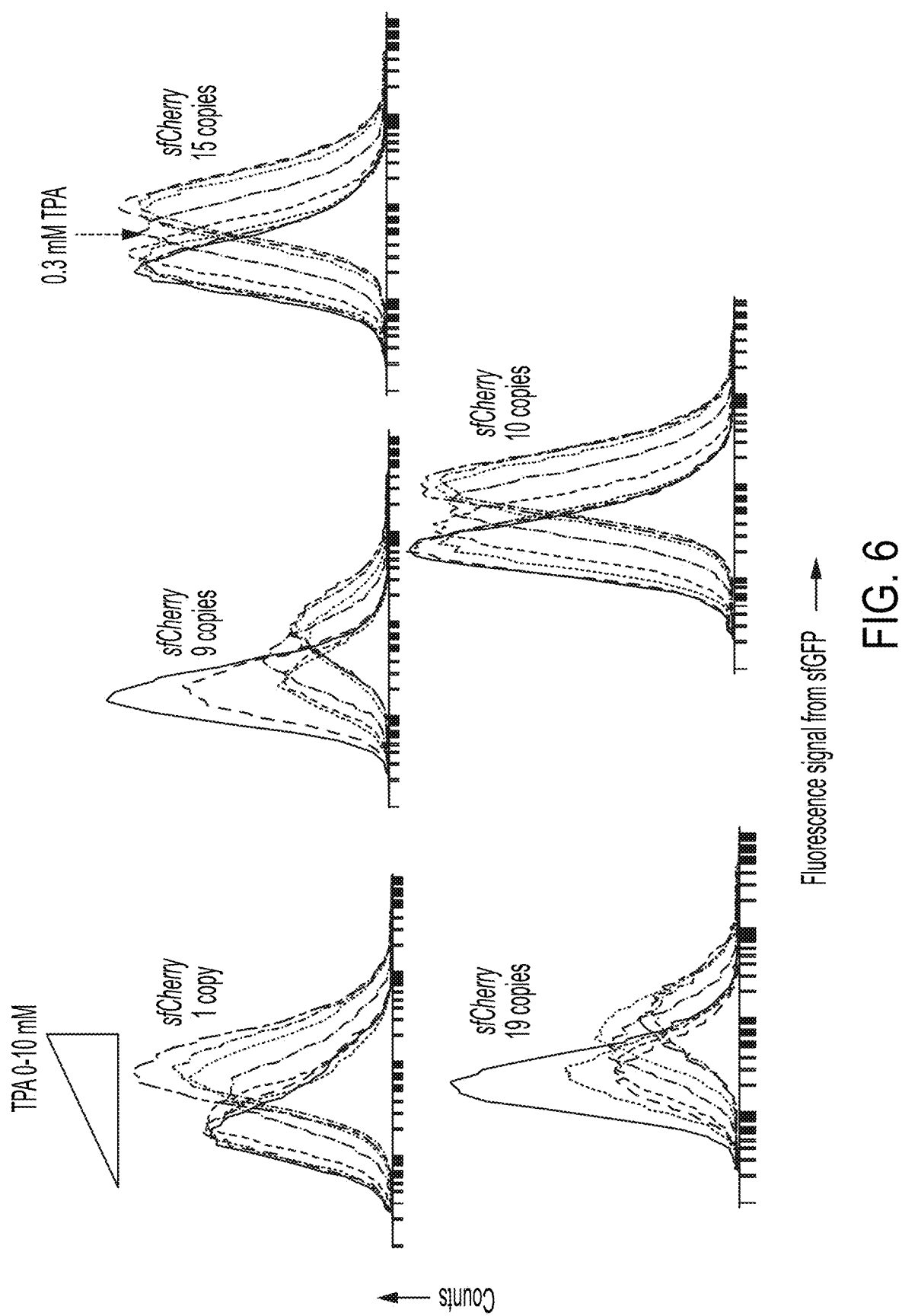
FIG. 6 shows signal from cells including pTPA3 and varying copy number of sfCherry in the presence of increasing amounts of TPA.

Different strains with varying copy number of the sfCherry (RFP) protein were constructed to test background and ratiometric signals based on gene dosage (RFP) and TPA concentration (GFP). Steady levels of fluorescence were detected from strains having multiple copies of RFP in conditions of 0 mM and 1 mM TPA (FIG. 5). In a parallel test, regardless of the number of RFP genes, the dose response of pTPA3 was conserved (FIG. 6).

Figure 8:
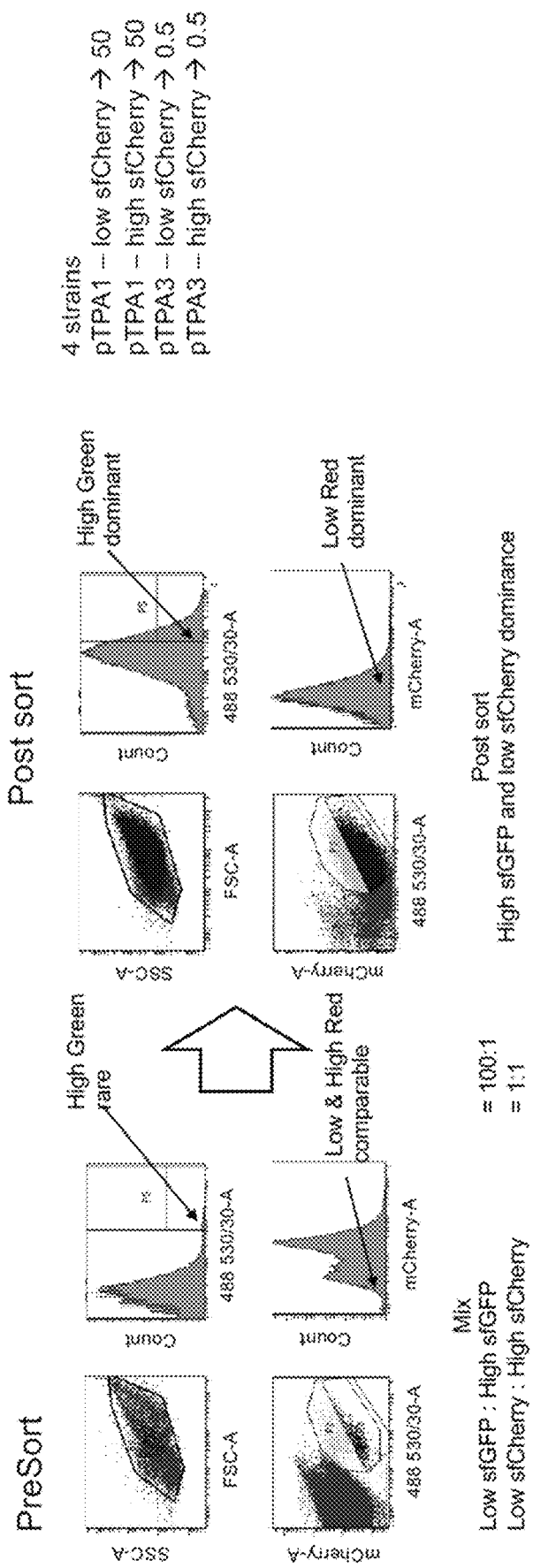
FIG. 8 shows detection of TPA in ADP1 strains expressing pTPA1 or pTPA3 by flow cytometry.

Four ADP1 strains were constructed. High sfCherry expressing strain (15 copies) with pTPA1 and pTPA3, and low sfCherry expressing strain (single copy) with pTPA1 and pTPA3. These four strains were mixed in a ratio 50:50:0.5:0.5 (pTPA1-low sfCherry: pTPA1-high sfCherry: pTPA3-low sfCherry:pTPA3-high sfCherry) and induced with 3 mM of TPA. Using FACS Aria III sorter population in the scatter plot that showed low red and high green. Post sorting, the population showed high green and low red dominant population (FIG. 8).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A terephthalic acid (TPA) biosensor comprising a nucleic acid encoding a TPA responsive transcription factor from *Comamonas testosteroni* (TphR) protein, a TphR regulated promoter comprising the nucleic acid sequence of nucleotides 4-114 of SEQ ID NO: 12, and a nucleic acid encoding a reporter protein operably linked to the promoter.

2. The TPA biosensor of claim 1, wherein the reporter protein is a fluorescent protein.

3. The TPA biosensor of claim 2, wherein the biosensor comprises a nucleic acid sequence with at least 95% sequence identity to nucleotides 2862-4457 of SEQ ID NO: 1 or the reverse complement thereof.

4. The TPA biosensor of claim 3, wherein the biosensor comprises the nucleic acid sequence of nucleotides 2862-4457 of SEQ ID NO: 1 or the reverse complement thereof.

5. The TPA biosensor of claim 4, wherein the biosensor consists of the nucleic acid sequence of nucleotides 2862-4457 of SEQ ID NO: 1 or the reverse complement thereof.

6. A vector or a host cell comprising the TPA biosensor of claim 1.

7. The vector of claim 6, wherein the vector comprises a nucleic acid sequence with at least 95% sequence identity to nucleotides 2862-4457 of SEQ ID NO: 1 or the reverse complement thereof.

8. The vector of claim 7, wherein the vector comprises the nucleic acid sequence of nucleotides 2862-4457 of SEQ ID NO: 1 or the reverse complement thereof.

9. The vector of claim 6, wherein the vector comprises the nucleic acid sequence of SEQ ID NO: 1 or SEQ ID NO: 2.

10. The host cell of claim 6, wherein the cell is a bacterial cell.

11. The host cell of claim 10, wherein the bacterial cell is an *Acinetobacter baylyi* cell.

12. The host cell of claim 11, wherein the *Acinetobacter baylyi* cell is an *A. baylyi* ADP1 cell.

13. A nucleic acid comprising the nucleic acid sequence of nucleotides 4-114 of SEQ ID NO: 12, encoding a terephthalic acid responsive transcription factor from *Comamonas testosteroni* (TphR) regulated promoter.

* * * * *

UNITED STATES PATENT AND TRADEMARK OFFICE
CERTIFICATE OF CORRECTION

PATENT NO. : 12,281,353 B1  
APPLICATION NO. : 17/173065  
DATED : April 22, 2025  
INVENTOR(S) : Ramesh K. Jha et al.

Page 1 of 1

It is certified that error appears in the above-identified patent and that said Letters Patent is hereby corrected as shown below:

On the Title Page

In Column 1, item (71), Applicants, Line 3, delete "Foundation Inc.," and insert -- Foundation, Inc., --, therefor.

In Column 1, item (73), Assignees, Line 2, delete "Los Alamos (MX);" and insert -- Los Alamos, NM (US); --, therefor.

Signed and Sealed this  
Seventh Day of October, 2025

John A. Squires  
*Director of the United States Patent and Trademark Office*

SEQUENCE LISTING

<160> NUMBER OF SEQ ID NOS: 18

<210> SEQ ID NO 1
<211> LENGTH: 4492
<212> TYPE: DNA
<213> ORGANISM: Artificial Sequence
<220> FEATURE:
<223> OTHER INFORMATION: TPA biosensor vector sequence

<400> SEQUENCE: 1

```
tagcggccgc tgcaggcctc agggcccgat cgatgccgcc gcttaattaa ttaatccaga      60
ggcatcaaat aaaacgaaag gctcagtcga aagactgggc ctttcgtttt atctgttgtt     120
tgtcggtgaa cgctctcctg agtaggacaa atccgccgcc ctagacctag tgtcatttta     180 tttccccgt tcagcatca agaacctttg cataacttgc tctatatcca cactgataat      240
tgccctcaaa ccataatcta aaggcgctag agtttgttga aacaatatct tttacatcat     300
tcgtatttaa aattccaaac tccgctcccc taaggcgaat aaaagccatt aaatcttttg     360
tatttaccaa attatagtca tccactatat ctaagagtaa attcttcaat tctctttttt     420
ggctttcatc aagtgttata tagcggtcaa tatcaaaatc attaatgttc aaaatatctt     480
ttttgtcgta tatatgttta ttcttagcaa tagcgtcctt tgattcatga gtcaaatatt     540
catatgaacc tttgatataa tcaagtatct caacatgagc aactgaacta ttccccaatt     600
ttcgcttaat cttgttccta acgctttcta ttgttacagg atttcgtgca atatatataa     660
cgtgatagtg tggtttttta tagtgctttc catttcgtat aacatcacta ctattccatg     720
tatctttatc ttttttttcg tccatatcgt gtaaaggact gacagccata gatacgccca     780
aactctctaa ttttttcttc caatcattag gaattgagtc aggatataat aaaaatccaa     840
aatttctagc tttagtattt taatagcca tgatataatt accttatcaa aaacaagtag     900
cgaaaactcg tatccttcta aaaacgcgag ctttcgctta ttttttttgt tctgattcct     960
ttcttgcata ttcttctata gctaacgccg caaccgcaga ttttgaaaaa ccttttttgtt    1020 tcgccatatc tgttaatttt ttatcttgct cttttgtcag agaaatcata actcttttttt    1080 tcgattctga aatcaccatt taaaaaactc caatcaaata attttataaa gttagtgtat    1140
cactttgtaa tcataaaaac aacaataaag ctacttaaat atagatttat aaaaaacgtt    1200
ggcgaaaacg ttggcgattc gttggcgatt gaaaaacccc ttaaaccctt gagccagttg    1260
ggatagagcg ttttttggcac aaaaattggc actcggcact taatggggggg tcgtagtacg    1320 gaagcaaaat tcgcttcctt tccccccatt tttttccaaa ttccagattt ttttcaaaaa    1380
ttttccagcg ctaccgctcg gcaaaattgc aagcaatttt taaaatcaaa cccatgaggg    1440
aatttcattc cctcatactc ccttgagcct cctccaaccg aaatagaagg gcgctgcgct    1500
tattatttca ttcagtcatc ggctttcata atctaacaga caacatcttc gctgcaaagc    1560 cacgctacg tcaagggctt ttacgctacg ataacgcctg ttttaacgat tatgccgata    1620
actaaacgaa ataaacgcta aaacgtctca gaaacgatt tgagacgttt taataaaaaa    1680
tcgcctagtg cttggattct caccaataaa aaacgcccgg cggcaaccga gcgttctgaa    1740
caaatccaga tggagttctg aggtcattac tggatctatc aacgggagtc caagcgagct    1800
```

```
cagccaatcg actggcgagc ggcatcttat ttgccgacta ccttggtgat ctcgcctttc    1860
acgtagtgga caaattcttc caactgatct gcgcgcgagg ccaagcgatc ttcttcttgt    1920
ccaagataag cctgtctagc ttcaagtatg acgggctgat actgggccgg caggcgctcc    1980
attgcccagt cggcagcgac atccttcggc gcgattttgc cggttactgc gctgtaccaa    2040
atgcgggaca acgtaagcac tacatttcgc tcatcgccag cccagtcggg cggcgagttc    2100
catagcgtta aggtttcatt tagcgcctca aatagatcct gttcaggaac cggatcaaag    2160
agttcctccg ccgctggacc taccaaggca acgctatgtt ctcttgcttt tgtcagcaag    2220
atagccagat caatgtcgat cgtggctggc tcgaagatac ctgcaagaat gtcattgcgc    2280
tgccattctc caaattgcag ttcgcgctta gctggataac gccacggaat gatgtcgtcg    2340
tgcacaacaa tggtgacttc tacagcgcgg agaatctcgc tctctccagg ggaagccgaa    2400
gtttccaaaa ggtcgttgat caaagctcgc cgcgttgttt catcaagcct tacggtcacc    2460
gtaaccagca aatcaatatc actgtgtggc ttcaggccgc catccactgc ggagccgtac    2520
aaatgtacgg ccagcaacgt cggttcgaga tggcgctcga tgacgccaac tacctctgat    2580
agttgagtcg atacttcggc gatcaccgct tccctcatga cattgcactc caccgctgat    2640
gacatcagtc gatcatagca cgatcaacgg cactgttgca aatagtcggt ggtgataaac    2700
ttatcatccc cttttgctga tggagctgca catgaactcg agtagggata acagggtaat    2760
agatctaagc ttctgcaggt cgactctaga cggatccccc tcaagtcaaa agcctccggt    2820
cggaggcttt tgactttctg ctatggaggt caggtatgat tctacaaccc ctgcggatat    2880
agcttttttt ccaactcatt gcgagcgcgc ttcagcggta tcaaaaagt ctccttgaac    2940 tcactcatgc tgagtctctc tgccctaact gcaatgctca tagcagcaat tgtgttgcct    3000
tgagggtcgc gcactggcgc tgccatagag cgcaccccca gctccagctc tccgtcgctg    3060
catgaccacc ctgattgccg gcaagtttca agcagaccta gcagctcctc caagtcagtc    3120
accgtatgag gggtcagtgc cacccgctcg atcatctcta gccttgcacg cgcctcctgt    3180
tgggggagtc ctgacaacag catccgacca atcgcagagc agtacaccgg caacctagat    3240
cctattccta ggcccgtgct caagctgcgc cgtgcggtcg aacgaccaat gatgatggca    3300
tcgtcctcca acaaagtacc aagcgaagcg gattccctgg tgcgctccga cagtgcatcc    3360
agtagtggct gggccaatgc aggcatgggg cgcgatgaca gaaatgaata ggcgatcagc    3420
agcgatttgg gctgcatcca gaacagtttg ccgtcgctct ctagatagcc aagctgtacc    3480
agtgtgctga gcgaacgtct ggcggatgct ggcgtggact gcgtgagcct ggctacctct    3540
gacagcgtca gccgggtatg ccgacggtca aagcaagtca gtaccccaa tcccttgcgc    3600 agcgattcca caaagttctt gtcctgcata gcgatcaaat caaggtgttt tcaacatttt    3660
tgcgcatagc gcaaaaacag tgtacaccaa agtacgacat ccttacaatg cagttcccca    3720
cacaagaagg agatatacat atggctagca aaggagaaga acttttcacg ggagttgtcc    3780
caattcttgt tgaattagat ggtgatgtta atgggcacaa attttctgtc cgtggagagg    3840
gtgaaggtga tgctacaaac ggaaaactca cccttaaatt tatttgcact actggaaaac    3900
tacctgttcc atggccaaca cttgtcacta ctctgaccta tggtgttcaa tgcttttccc    3960
gttatccgga tcacatgaaa cggcatgact ttttcaagag tgccatgccc gaaggttatg    4020
tacaggaacg cactatatct ttcaaagatg acgggaccta caagacgcgt gctgaagtca    4080
agtttgaagg tgatacccct gttaatcgta tcgagttaaa gggtattgat tttaagaag    4140 atggaaacat tcttggacac aaactcgagt acaactttaa ctcacacaat gtatacatca    4200
```

```
cggcagacaa acaaaagaat ggaatcaaag ctaacttcaa aattcgccac aacgttgaag    4260
atggttccgt tcaactagca gaccattatc aacaaaatac tccaattggc gatggccctg    4320
tccttttacc agacaaccat tacctgtcga cacaatctgt cctttcgaaa gatcccaacg    4380
aaaagcgtga ccacatggtc cttcttgagt ttgtaactgc tgctgggatt acacatggca    4440
tggatgagct ctacaaaggt ggcggttctg aattcacacc taggtaaact ag            4492

<210> SEQ ID NO 2
<211> LENGTH: 4492
<212> TYPE: DNA
<213> ORGANISM: Artificial Sequence
<220> FEATURE:
<223> OTHER INFORMATION: TPA biosensor vector, reverse complement

<400> SEQUENCE: 2
ctagtttacc taggtgtgaa ttcagaaccg ccacctttgt agagctcatc catgccatgt      60
gtaatcccag cagcagttac aaactcaaga aggaccatgt ggtcacgctt ttcgttggga    120
tctttcgaaa ggacagattg tgtcgacagg taatggttgt ctggtaaaag gacagggcca    180
tcgccaattg gagtattttg ttgataatgg tctgctagtt gaacggaacc atcttcaacg    240
ttgtggcgaa ttttgaagtt agctttgatt ccattctttt gtttgtctgc cgtgatgtat    300
acattgtgtg agttaaagtt gtactcgagt ttgtgtccaa gaatgtttcc atcttcttta    360
aaatcaatac cctttaactc gatacgatta acaagggtat caccttcaaa cttgacttca    420
gcacgcgtct tgtaggtccc gtcatctttg aaagatatag tgcgttcctg tacataacct    480
tcgggcatgg cactcttgaa aaagtcatgc cgtttcatgt gatccggata acgggaaaag    540
cattgaacac cataggtcag agtagtgaca agtgttggcc atggaacagg tagttttcca    600
gtagtgcaaa taaatttaag ggtgagtttt ccgtttgtag catcaccttc accctctcca    660
cggacagaaa atttgtgccc attaacatca ccatctaatt caacaagaat tgggacaact    720
cccgtgaaaa gttcttctcc tttgctagcc atatgtatat ctccttcttg tgtgggaac    780 tgcattgtaa ggatgtcgta ctttggtgta cactgttttt gcgctatgcg caaaaatgtt    840
gaaaacacct tgatttgatc gctatgcagg acaagaactt tgtggaatcg ctgcgcaagg    900 gattggggt actgacttgc tttgaccgtc ggcatacccg gctgacgctg tcagaggtag    960
ccaggctcac gcagtccacg ccagcatccg ccagacgttc gctcagcaca ctggtacagc   1020
ttggctatct agagagcgac ggcaaactgt tctggatgca gcccaaatcg ctgctgatcg   1080
cctattcatt tctgtcatcg cgccccatgc ctgcattggc ccagccacta ctggatgcac   1140
tgtcggagcg caccagggaa tccgcttcgc ttggtacttt gttggaggac gatgccatca   1200
tcattggtcg ttcgaccgca cggcgcagct tgagcacggg cctaggaata ggatctaggt   1260
tgccggtgta ctgctctgcg attggtcgga tgctgttgtc aggactcccc caacaggagg   1320
cgcgtgcaag gctagagatg atcgagcggg tggcactgac ccctcatacg gtgactgact   1380
tggaggagct gctaggtctg cttgaaactt gccggcaatc agggtggtca tgcagcgacg   1440
gagagctgga gctgggggtg cgctctatgg cagcgccagt gcgcgaccct caaggcaaca   1500
caattgctgc tatgagcatt gcagttaggg cagagagact cagcatgagt gagttcaagg   1560
agactttttt gataccgctg aagcgcgctc gcaatgagtt ggaaaaaaag ctatatccgc   1620
aggggttgta gaatcatacc tgacctccat agcagaaagt caaagcctc cgaccggagg   1680 cttttgactt gaggggatc cgtctagagt cgacctgcag aagcttagat ctattaccct   1740
```

```
gttatcccta ctcgagttca tgtgcagctc catcagcaaa agggatgat aagtttatca   1800 ccaccgacta tttgcaacag tgccgttgat cgtgctatga tcgactgatg tcatcagcgg   1860
tggagtgcaa tgtcatgagg gaagcggtga tcgccgaagt atcgactcaa ctatcagagg   1920
tagttggcgt catcgagcgc catctcgaac cgacgttgct ggccgtacat tgtacggct    1980 ccgcagtgga tggcggcctg aagccacaca gtgatattga tttgctggtt acggtgaccg   2040
taaggcttga tgaaacaacg cggcgagctt tgatcaacga ccttttggaa acttcggctt   2100
cccctggaga gagcgagatt ctccgcgctg tagaagtcac cattgttgtg cacgacgaca   2160
tcattccgtg gcgttatcca gctaagcgcg aactgcaatt tggagaatgg cagcgcaatg   2220
acattcttgc aggtatcttc gagccagcca cgatcgacat tgatctggct atcttgctga   2280
caaaagcaag agaacatagc gttgccttgg taggtccagc ggcggaggaa ctctttgatc   2340
cggttcctga acaggatcta tttgaggcgc taaatgaaac cttaacgcta tggaactcgc   2400
cgcccgactg ggctggcgat gagcgaaatg tagtgcttac gttgtcccgc atttggtaca   2460
gcgcagtaac cggcaaaatc gcgccgaagg atgtcgctgc cgactgggca atggagcgcc   2520
tgccggccca gtatcagccc gtcatacttg aagctagaca ggcttatctt ggacaagaag   2580
aagatcgctt ggcctcgcgc gcagatcagt tggaagaatt tgtccactac gtgaaggcg    2640 agatcaccaa ggtagtcggc aaataagatg ccgctcgcca gtcgattggc tgagctcgct   2700
tggactcccg ttgatagatc cagtaatgac ctcagaactc catctggatt tgttcagaac   2760
gctcggttgc cgccgggcgt ttttattgg tgagaatcca agcactaggc gatttttat    2820 taaaacgtct caaaatcgtt tctgagacgt tttagcgttt atttcgttta gttatcggca   2880
taatcgttaa aacaggcgtt atcgtagcgt aaaagccctt gagcgtagcg tggctttgca   2940
gcgaagatgt tgtctgttag attatgaaag ccgatgactg aatgaaataa taagcgcagc   3000
gcccttctat ttcggttgga ggaggctcaa gggagtatga gggaatgaaa ttccctcatg   3060
ggtttgattt taaaaattgc ttgcaatttt gccgagcggt agcgctggaa aattttttgaa  3120 aaaaatctgg aatttggaaa aaaatggggg gaaaggaagc gaattttgct tccgtactac   3180
gaccccccat taagtgccga gtgccaattt tgtgccaaa aacgctctat cccaactggc    3240
tcaagggttt aaggggtttt tcaatcgcca acgaatcgcc aacgttttcg ccaacgtttt   3300
ttataaatct atatttaagt agctttattg ttgtttttat gattacaaag tgatacacta   3360
actttataaa attatttgat tggagttttt taaatggtga tttcagaatc gaaaaaaaga   3420
gttatgattt ctctgacaaa agagcaagat aaaaaattaa cagatatggc gaaacaaaaa   3480 ggttttcaa atctgcggt tgcggcgtta gctatagaag aatatgcaag aaaggaatca    3540
gaacaaaaaa aataagcgaa agctcgcgtt tttagaagga tacgagtttt cgctacttgt   3600
ttttgataag gtaattatat catggctatt aaaaatacta aagctagaaa ttttggattt   3660
ttattatatc ctgactcaat tcctaatgat tggaaggaaa aattagagag tttgggcgta   3720
tctatggctg tcagtccttt acacgatatg gacgaaaaaa aagataaaga tacatggaat   3780
agtagtgatg ttatacgaaa tggaaagcac tataaaaaac cacactatca cgttatatat   3840
attgcacgaa atcctgtaac aatagaaagc gttaggaaca agattaagcg aaaattgggg   3900
aatagttcag ttgctcatgt tgagatactt gattatatca aaggttcata tgaatatttg   3960
actcatgaat caaggacgc tattgctaag aataaacata tatacgacaa aaagatatt    4020 ttgaacatta atgattttga tattgaccgc tatataacac ttgatgaaag ccaaaaaaga   4080
gaattgaaga atttactctt agatatagtg gatgactata atttggtaaa tacaaaagat   4140
```

```
ttaatggctt ttattcgcct taggggagcg gagtttggaa ttttaaatac gaatgatgta    4200
aaagatattg tttcaacaaa ctctagcgcc tttagattat ggtttgaggg caattatcag    4260
tgtggatata gagcaagtta tgcaaaggtt cttgatgctg aaacggggga aataaaatga    4320
cactaggtct agggcggcgg atttgtccta ctcaggagag cgttcaccga caacaacag     4380 ataaaacgaa aggcccagtc tttcgactga gcctttcgtt ttatttgatg cctctggatt    4440
aattaattaa gcggcggcat cgatcgggcc ctgaggcctg cagcggccgc ta            4492
```

<210> SEQ ID NO 3
<211> LENGTH: 239
<212> TYPE: PRT
<213> ORGANISM: Artificial Sequence
<220> FEATURE:
<223> OTHER INFORMATION: superfolder GFP protein

<400> SEQUENCE: 3

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Val Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235
```

<210> SEQ ID NO 4
<211> LENGTH: 255
<212> TYPE: PRT
<213> ORGANISM: Comamonas testosteroni

<400> SEQUENCE: 4

```
Met Gln Asp Lys Asn Phe Val Glu Ser Leu Arg Lys Gly Leu Gly Val
1               5                   10                  15
```

```
Leu Thr Cys Phe Asp Arg Arg His Thr Arg Leu Thr Leu Ser Glu Val
            20                  25                  30

Ala Arg Leu Thr Gln Ser Thr Pro Ala Ser Ala Arg Arg Ser Leu Ser
        35                  40                  45

Thr Leu Val Gln Leu Gly Tyr Leu Glu Ser Asp Gly Lys Leu Phe Trp
 50                  55                  60

Met Gln Pro Lys Ser Leu Leu Ile Ala Tyr Ser Phe Leu Ser Ser Arg
 65                  70                  75                  80

Pro Met Pro Ala Leu Ala Gln Pro Leu Leu Asp Ala Leu Ser Glu Arg
                85                  90                  95

Thr Arg Glu Ser Ala Ser Leu Gly Thr Leu Leu Glu Asp Asp Ala Ile
            100                 105                 110

Ile Ile Gly Arg Ser Thr Ala Arg Arg Ser Leu Ser Thr Gly Leu Gly
            115                 120                 125

Ile Gly Ser Arg Leu Pro Val Tyr Cys Ser Ala Ile Gly Arg Met Leu
        130                 135                 140

Leu Ser Gly Leu Pro Gln Gln Glu Ala Arg Ala Arg Leu Glu Met Ile
145                 150                 155                 160

Glu Arg Val Ala Leu Thr Pro His Thr Val Thr Asp Leu Glu Glu Leu
                165                 170                 175

Leu Gly Leu Leu Glu Thr Cys Arg Gln Ser Gly Trp Ser Cys Ser Asp
            180                 185                 190

Gly Glu Leu Glu Leu Gly Val Arg Ser Met Ala Ala Pro Val Arg Asp
        195                 200                 205

Pro Gln Gly Asn Thr Ile Ala Ala Met Ser Ile Ala Val Arg Ala Glu
 210                 215                 220

Arg Leu Ser Met Ser Glu Phe Lys Glu Thr Phe Leu Ile Pro Leu Lys
225                 230                 235                 240

Arg Ala Arg Asn Glu Leu Glu Lys Lys Leu Tyr Pro Gln Gly Leu
                245                 250                 255

<210> SEQ ID NO 5
<211> LENGTH: 263
<212> TYPE: PRT
<213> ORGANISM: Artificial Sequence
<220> FEATURE:
<223> OTHER INFORMATION: SmR protein

<400> SEQUENCE: 5

Met Arg Glu Ala Val Ile Ala Glu Val Ser Thr Gln Leu Ser Glu Val
1               5                   10                  15

Val Gly Val Ile Glu Arg His Leu Glu Pro Thr Leu Leu Ala Val His
            20                  25                  30

Leu Tyr Gly Ser Ala Val Asp Gly Gly Leu Lys Pro His Ser Asp Ile
        35                  40                  45

Asp Leu Leu Val Thr Val Thr Val Arg Leu Asp Glu Thr Thr Arg Arg
 50                  55                  60

Ala Leu Ile Asn Asp Leu Leu Glu Thr Ser Ala Ser Pro Gly Glu Ser
65                  70                  75                  80

Glu Ile Leu Arg Ala Val Glu Val Thr Ile Val Val His Asp Asp Ile
                85                  90                  95

Ile Pro Trp Arg Tyr Pro Ala Lys Arg Glu Leu Gln Phe Gly Glu Trp
            100                 105                 110

Gln Arg Asn Asp Ile Leu Ala Gly Ile Phe Glu Pro Ala Thr Ile Asp
        115                 120                 125
```

```
Ile Asp Leu Ala Ile Leu Leu Thr Lys Ala Arg Glu His Ser Val Ala
            130                 135                 140

Leu Val Gly Pro Ala Ala Glu Glu Leu Phe Asp Pro Val Pro Glu Gln
145                 150                 155                 160

Asp Leu Phe Glu Ala Leu Asn Glu Thr Leu Thr Leu Trp Asn Ser Pro
                165                 170                 175

Pro Asp Trp Ala Gly Asp Glu Arg Asn Val Val Leu Thr Leu Ser Arg
                180                 185                 190

Ile Trp Tyr Ser Ala Val Thr Gly Lys Ile Ala Pro Lys Asp Val Ala
            195                 200                 205

Ala Asp Trp Ala Met Glu Arg Leu Pro Ala Gln Tyr Gln Pro Val Ile
            210                 215                 220

Leu Glu Ala Arg Gln Ala Tyr Leu Gly Gln Glu Glu Asp Arg Leu Ala
225                 230                 235                 240

Ser Arg Ala Asp Gln Leu Glu Glu Phe Val His Tyr Val Lys Gly Glu
                245                 250                 255

Ile Thr Lys Val Val Gly Lys
            260

<210> SEQ ID NO 6
<211> LENGTH: 17
<212> TYPE: PRT
<213> ORGANISM: Artificial Sequence
<220> FEATURE:
<223> OTHER INFORMATION: Factor Xa sequence

<400> SEQUENCE: 6

Ile Glu Gly Arg Cys Ala Tyr Tyr Phe Ile Gln Ser Ser Ala Phe Ile
1               5                   10                  15

Ile

<210> SEQ ID NO 7
<211> LENGTH: 69
<212> TYPE: PRT
<213> ORGANISM: Artificial Sequence
<220> FEATURE:
<223> OTHER INFORMATION: Hypothetical protein

<400> SEQUENCE: 7

Met Gly Gly Lys Glu Ala Asn Phe Ala Ser Val Leu Arg Pro Pro Ile
1               5                   10                  15

Lys Cys Arg Val Pro Ile Phe Val Pro Lys Thr Leu Tyr Pro Asn Trp
                20                  25                  30

Leu Lys Gly Leu Arg Gly Phe Ser Ile Ala Asn Glu Ser Pro Thr Phe
            35                  40                  45

Ser Pro Thr Phe Phe Ile Asn Leu Tyr Leu Ser Ser Phe Ile Val Val
        50                  55                  60

Phe Met Ile Thr Lys
65

<210> SEQ ID NO 8
<211> LENGTH: 53
<212> TYPE: PRT
<213> ORGANISM: Artificial Sequence
<220> FEATURE:
<223> OTHER INFORMATION: Hypothetical protein

<400> SEQUENCE: 8

Met Val Ile Ser Glu Ser Lys Lys Arg Val Met Ile Ser Leu Thr Lys
1               5                   10                  15
```

Glu Gln Asp Lys Lys Leu Thr Asp Met Ala Lys Gln Lys Gly Phe Ser
            20                  25                  30

Lys Ser Ala Val Ala Ala Leu Ala Ile Glu Glu Tyr Ala Arg Lys Glu
            35                  40                  45

Ser Glu Gln Lys Lys
        50

<210> SEQ ID NO 9
<211> LENGTH: 232
<212> TYPE: PRT
<213> ORGANISM: Artificial Sequence
<220> FEATURE:
<223> OTHER INFORMATION: RepA sequence

<400> SEQUENCE: 9

Met Ala Ile Lys Asn Thr Lys Ala Arg Asn Phe Gly Phe Leu Leu Tyr
1               5                   10                  15

Pro Asp Ser Ile Pro Asn Asp Trp Lys Glu Lys Leu Glu Ser Leu Gly
            20                  25                  30

Val Ser Met Ala Val Ser Pro Leu His Asp Met Asp Glu Lys Lys Asp
            35                  40                  45

Lys Asp Thr Trp Asn Ser Ser Asp Val Ile Arg Asn Gly Lys His Tyr
        50                  55                  60

Lys Lys Pro His Tyr His Val Ile Tyr Ile Ala Arg Asn Pro Val Thr
65                  70                  75                  80

Ile Glu Ser Val Arg Asn Lys Ile Lys Arg Lys Leu Gly Asn Ser Ser
                85                  90                  95

Val Ala His Val Glu Ile Leu Asp Tyr Ile Lys Gly Ser Tyr Glu Tyr
            100                 105                 110

Leu Thr His Glu Ser Lys Asp Ala Ile Ala Lys Asn Lys His Ile Tyr
            115                 120                 125

Asp Lys Lys Asp Ile Leu Asn Ile Asn Asp Phe Asp Ile Asp Arg Tyr
        130                 135                 140

Ile Thr Leu Asp Glu Ser Gln Lys Arg Glu Leu Lys Asn Leu Leu Leu
145                 150                 155                 160

Asp Ile Val Asp Asp Tyr Asn Leu Val Asn Thr Lys Asp Leu Met Ala
                165                 170                 175

Phe Ile Arg Leu Arg Gly Ala Glu Phe Gly Ile Leu Asn Thr Asn Asp
            180                 185                 190

Val Lys Asp Ile Val Ser Thr Asn Ser Ser Ala Phe Arg Leu Trp Phe
            195                 200                 205

Glu Gly Asn Tyr Gln Cys Gly Tyr Arg Ala Ser Tyr Ala Lys Val Leu
        210                 215                 220

Asp Ala Glu Thr Gly Glu Ile Lys
225                 230

<210> SEQ ID NO 10
<211> LENGTH: 118
<212> TYPE: DNA
<213> ORGANISM: Artificial Sequence
<220> FEATURE:
<223> OTHER INFORMATION: TphR promoter region

<400> SEQUENCE: 10
catagcgatc aaatcaaggt gttttcaaca ttttttgcgca tagcgcaaaa acaggtttaa      60
cacaaagtac gacatcctca tactgcagtt ccccacacaa gaaggagata tacatatg      118

```
<210> SEQ ID NO 11
<211> LENGTH: 118
<212> TYPE: DNA
<213> ORGANISM: Artificial Sequence
<220> FEATURE:
<223> OTHER INFORMATION: TphR promoter region

<400> SEQUENCE: 11
catagcgatc aaatcaaggt gttttcaaca ttttgcgca tagcgcaaaa acaggtttaa      60
cacaaagtac gacatcctta caatgcagtt ccccacacaa gaaggagata tacatatg     118

<210> SEQ ID NO 12
<211> LENGTH: 117
<212> TYPE: DNA
<213> ORGANISM: Artificial Sequence
<220> FEATURE:
<223> OTHER INFORMATION: TphR promoter region

<400> SEQUENCE: 12
catagcgatc aaatcaaggt gttttcaaca ttttgcgca tagcgcaaaa acagtgtaca      60
ccaaagtacg acatccttac aatgcagttc cccacacaag aaggagatat acatatg      117

<210> SEQ ID NO 13
<211> LENGTH: 280
<212> TYPE: DNA
<213> ORGANISM: Artificial sequence
<220> FEATURE:
<223> OTHER INFORMATION: Synthetic construct

<400> SEQUENCE: 13
ggcggatgct ggcgtggact gcgtgagcct ggctacctct gacagcgtca gccgggtatg      60
ccgacggtca aagcaagtca gtaccccaa tcccttgcgc agcgattcca caaagttctt     120
gtcctgcata gcgatcaaat caaggtgttt tcaacatttt tgcgcatagc gcaaaaacag     180
gtttaacaca agtacgaca tccttacaat gcagttcccc acacaagaag gagatataca     240
tatggctagc aaaggagaag aacttttcac gggagttgtc                          280

<210> SEQ ID NO 14
<211> LENGTH: 280
<212> TYPE: DNA
<213> ORGANISM: Artificial sequence
<220> FEATURE:
<223> OTHER INFORMATION: Synthetic construct

<400> SEQUENCE: 14
gacaactccc gtgaaaagtt cttctccttt gctagccata tgtatatctc cttcttgtgt      60
ggggaactgc attgtaagga tgtcgtactt tgtgttaaac ctgttttgc gctatgcgca     120 aaaatgttga aaacaccttg atttgatcgc tatgcaggac aagaactttg tggaatcgct     180
gcgcaaggga ttgggggtac tgacttgctt tgaccgtcgg catacccggc tgacgctgtc     240
agaggtagcc aggctcacgc agtccacgcc agcatccgcc                          280

<210> SEQ ID NO 15
<211> LENGTH: 47
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (25)..(30)
<223> OTHER INFORMATION: Unknown
```

```
<400> SEQUENCE: 15
gtttaacaca aagtacgaca tcctnnnnnn gcagttcccc acacaag         47

<210> SEQ ID NO 16
<211> LENGTH: 9
<212> TYPE: PRT
<213> ORGANISM: Artificial sequence
<220> FEATURE:
<223> OTHER INFORMATION: Synthetic construct

<400> SEQUENCE: 16

Gly Gly Gly Ser Glu Phe Thr Pro Arg
1               5

<210> SEQ ID NO 17
<211> LENGTH: 23
<212> TYPE: DNA
<213> ORGANISM: Artificial sequence
<220> FEATURE:
<223> OTHER INFORMATION: Synthetic construct

<400> SEQUENCE: 17
caaagtacga catccttaca atg                                  23

<210> SEQ ID NO 18
<211> LENGTH: 36
<212> TYPE: DNA
<213> ORGANISM: Artificial sequence
<220> FEATURE:
<223> OTHER INFORMATION: Synthetic construct

<400> SEQUENCE: 18
aaggagatat acatatggct agcaaaggag aagaac                    36
```